(12) United States Patent
Tripathi

(10) Patent No.: US 11,033,514 B2
(45) Date of Patent: Jun. 15, 2021

(54) MODIFIED RESVERATROL COMPOSITION AND USE THEREOF

(71) Applicant: Vinaykumar Tripathi, Thane (West) Maharashtra (IN)

(72) Inventor: Vinaykumar Tripathi, Thane (West) Maharashtra (IN)

(73) Assignee: Vinaykumar Tripathi, Thane (West) Maharashtra (IN)

( * ) Notice: Subject to any disclaimer, the term of this patent is extended or adjusted under 35 U.S.C. 154(b) by 42 days.

(21) Appl. No.: 16/328,915

(22) PCT Filed: Aug. 29, 2017

(86) PCT No.: PCT/IB2017/055174
§ 371 (c)(1),
(2) Date: Feb. 27, 2019

(87) PCT Pub. No.: WO2018/042324
PCT Pub. Date: Mar. 8, 2018

(65) Prior Publication Data
US 2019/0343775 A1   Nov. 14, 2019

Related U.S. Application Data

(60) Provisional application No. 62/380,986, filed on Aug. 29, 2016, provisional application No. 62/381,000, filed on Aug. 29, 2016, provisional application No. 62/381,009, filed on Aug. 29, 2016, provisional application No. 62/445,255, filed on Jan. 12, 2017, provisional application No. 62/445,257, filed on Jan. 12, 2017.

(30) Foreign Application Priority Data

Feb. 11, 2017   (WO) ................. PCT/IB2017/050767
May 31, 2017   (IN) ............................. 201721019179

(51) Int. Cl.
| | |
|---|---|
| A61K 31/05 | (2006.01) |
| A61K 9/50 | (2006.01) |
| A61K 36/48 | (2006.01) |
| A61K 9/00 | (2006.01) |
| A61K 36/60 | (2006.01) |

(52) U.S. Cl.
CPC ............ *A61K 31/05* (2013.01); *A61K 9/0065* (2013.01); *A61K 9/5015* (2013.01); *A61K 9/5063* (2013.01); *A61K 9/5084* (2013.01); *A61K 36/48* (2013.01); *A61K 36/60* (2013.01)

(58) Field of Classification Search
None
See application file for complete search history.

(56) References Cited

U.S. PATENT DOCUMENTS

| | | | |
|---|---|---|---|
| 8,465,757 B2 | 6/2013 | Duan et al. | |
| 8,815,936 B2 | 8/2014 | Grant et al. | |

FOREIGN PATENT DOCUMENTS

| | | |
|---|---|---|
| CN | 105016981 B | 11/2015 |
| KR | 100951706 B1 | 4/2010 |
| KR | 20130125687 A | 11/2019 |

OTHER PUBLICATIONS

Gurinder Singh and Roopa S. Pai, Recent Advances of Resveratrol in Nanostructured Based Delivery Systems and in the Management of HIV/AIDS Journal of Controlled Release, 2014 http://dx.doi.org/10.1016/j.jconrel.2014.09.002 p. 3, 4 10.

Yu-Tang Chin et al, Anti-proliferative and gene expression actions of resveratrol in breast cancer cells in vitro. Oncotarget, vol. 5, No. 24, Nov. 8, 2014. p. 2, coulmn left, para 2 and 3.

Ludovic Le Corre et al, Differential Expression of Genes Induced by Resveratrol in Human Breast Cancer Cell Lines. Nutrition and Cancer, 56(2), 193-203, 2006. abstract ,table 2.

*Primary Examiner* — Jessica Worsham
(74) *Attorney, Agent, or Firm* — Dilworth IP, LLC

(57) ABSTRACT

The present disclosure relates to a resveratrol delivery system having modified resveratrol composition wherein the active ingredient is stable colloidal resveratrol nanoparticles in unconjugated form. The said composition and its process thereof can be used in numerous applications for treatment of a mammal susceptible to or afflicted with insulin resistance, metabolic syndrome, aging, apoptosis, inflammation, stress resistance, cancer, cardiovascular disease, muscular dystrophy, low fertility rates or any combination thereof since the modified resveratrol composition has higher bioavailability and greater half-life.

20 Claims, 17 Drawing Sheets
Specification includes a Sequence Listing.

Figure 1: SEM analysis of Tree fat coated Resveratrol nanoparticles (A) 70,000 x (B) 1,50,000x

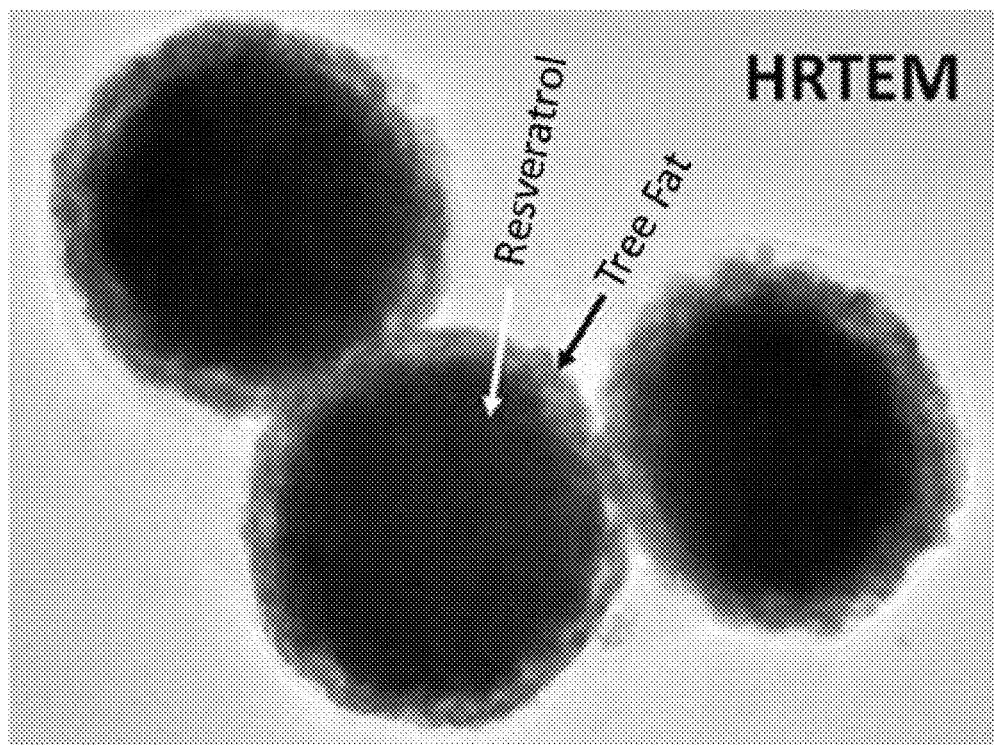
Figure 3: HR-TEM analysis of Tree fat coated Resveratrol nanoparticles (2,50,000X)

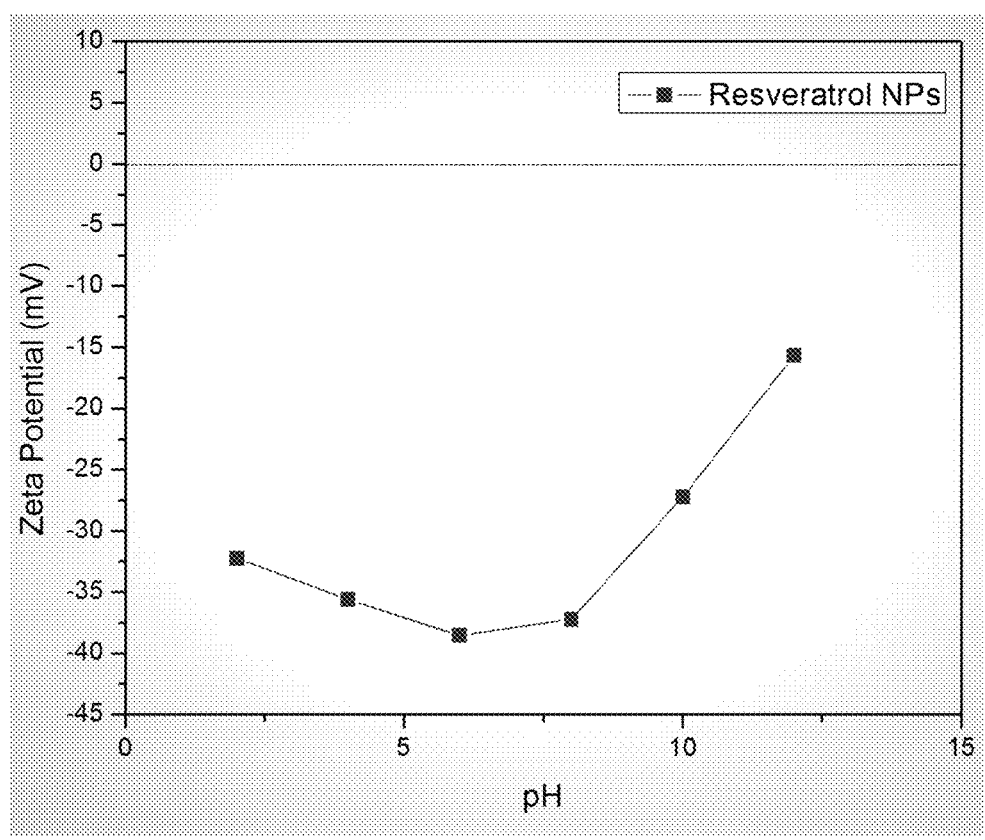
Figure 4: Zeta potential analysis of Resveratrol nanoparticles coated with tree fat

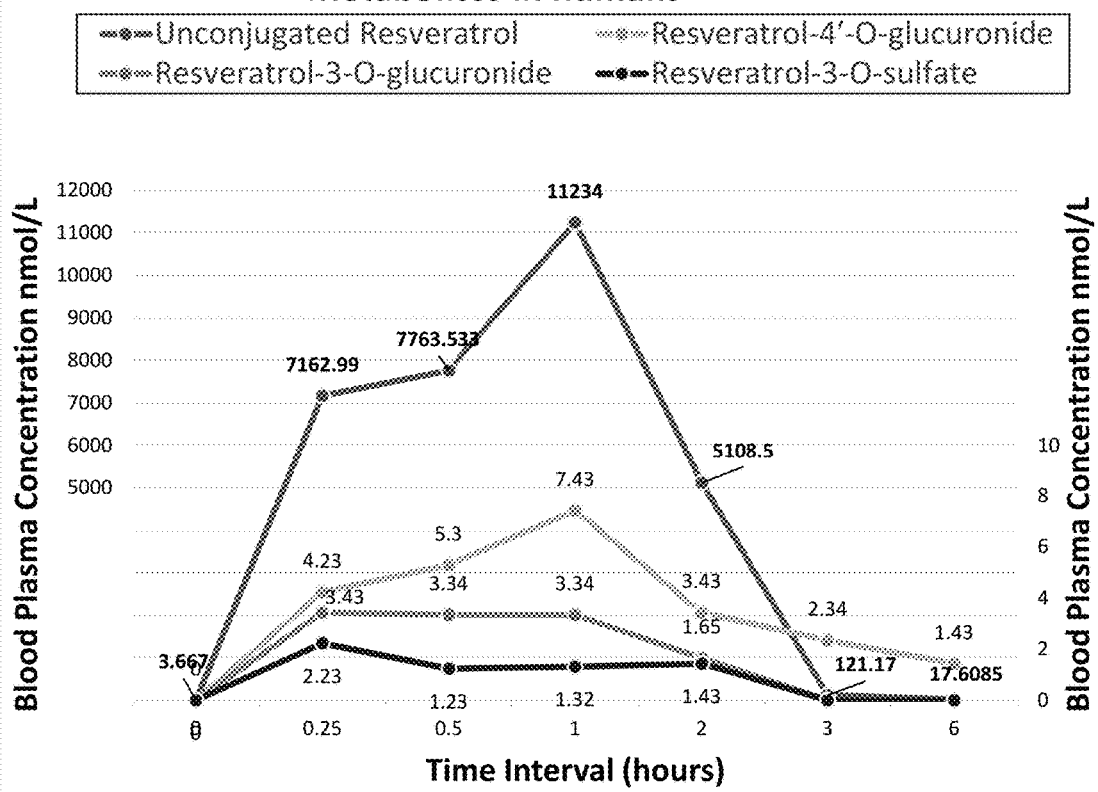
(A)
Figure 5: Bioavailability of orally administered resveratrol Mean Bioavailability of Resveratrol and its Metabolites in humans

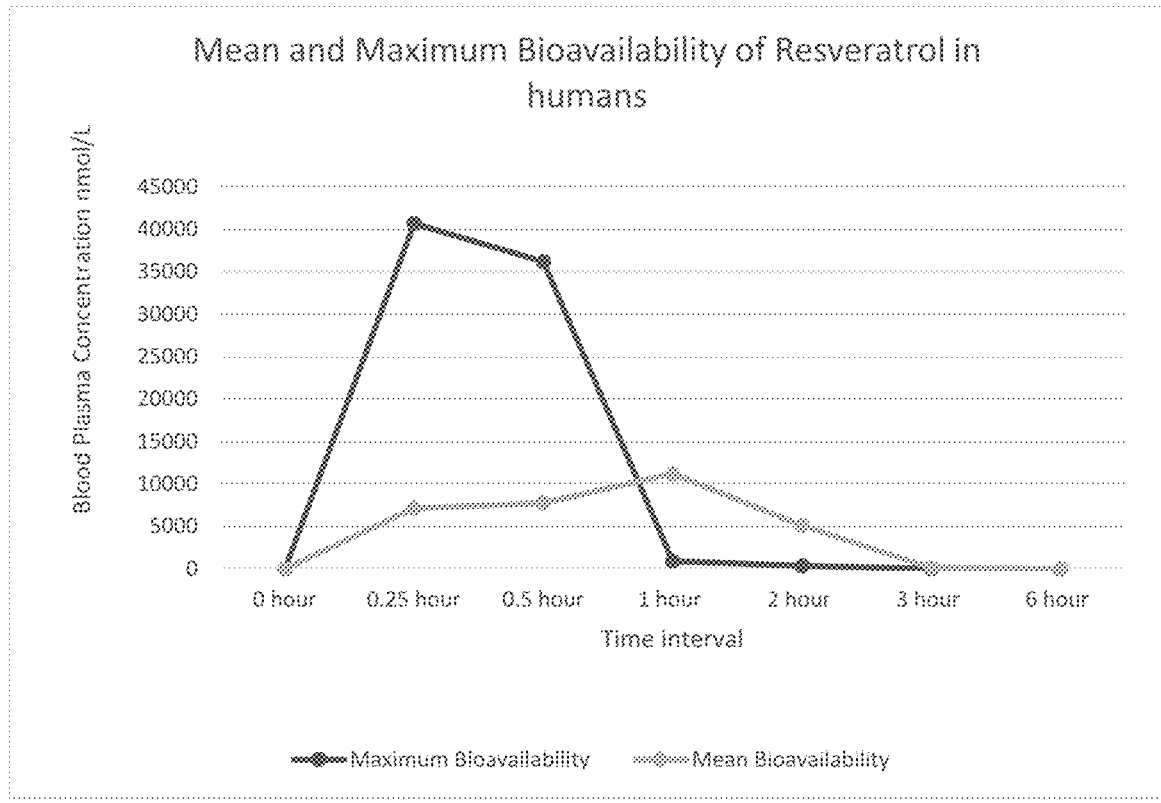
(B)
Figure 5: Mean and Maximum Bioavailability of Resveratrol in humans (B)

| Parameters | Volunteers | Modified Resveratrol treated | | | | | Placebo treated | | | | |
|---|---|---|---|---|---|---|---|---|---|---|---|
| | | 1 | 2 | 3 | 4 | 5 | 1 | 2 | 3 | 4 | 5 |
| Age (years) | | 27 | 35 | 34 | 30 | 57 | 29 | 39 | 33 | 32 | 55 |
| Total cholesterol (mg/dl) | Day 0 | 146 | 207 | 177 | 255 | 257 | 166 | 195 | 254 | 158 | 232 |
| | Day 15 | 116 | 169 | 136 | 194 | 204 | 189 | 191 | 261 | 178 | 244 |
| Triglycerides (mg/dl) | Day 0 | 60 | 71 | 146 | 148 | 149 | 69 | 104 | 123 | 117 | 165 |
| | Day 15 | 44 | 59 | 123 | 115 | 102 | 82 | 123 | 121 | 132 | 171 |
| HDL-C (mg/dl) | Day 0 | 62 | 36 | 35 | 34 | 42 | 39 | 43 | 55 | 39 | 43 |
| | Day 15 | 67 | 51 | 52 | 68 | 58 | 37 | 41 | 53 | 38 | 45 |
| LDL (mg/dl) | Day 0 | 103 | 157 | 113 | 199 | 195 | 147 | 169 | 152 | 201 | 178 |
| | Day 15 | 76 | 119 | 106 | 138 | 134 | 154 | 178 | 146 | 205 | 189 |
| VLDL (mg/dl) | Day 0 | 14 | 18 | 29 | 30 | 26 | 12 | 15 | 18 | 26 | 27 |
| | Day 15 | 9 | 12 | 25 | 23 | 18 | 13 | 19 | 27 | 25 | 30 |
| Fasting Insulin mIU/L | Day 0 | 10 | 6 | 25 | 19 | 43 | 12 | 11 | 25 | 15 | 23 |
| | Day 15 | 6 | 3 | 10 | 3 | 33 | 13 | 15 | 30 | 21 | 21 |

Figure 10

```
                         SEQUENCE LISTING

<160> NUMBER OF SEQ ID NOS: 38

<210> SEQ ID NO 1
<211> LENGTH: 20
<212> TYPE: DNA
<213> ORGANISM: Homo sapiens

<400> SEQUENCE: 1
agccctcatt tcaccaggcc                                                    20

<210> SEQ ID NO 2
<211> LENGTH: 20
<212> TYPE: DNA
<213> ORGANISM: Homo sapiens

<400> SEQUENCE: 2
tgggactcct ccgggttttg                                                    20

<210> SEQ ID NO 3
<211> LENGTH: 25
<212> TYPE: DNA
<213> ORGANISM: Homo sapiens

<400> SEQUENCE: 3
cttgctgcag aagtgggtgg aggaa                                              25

<210> SEQ ID NO 4
<211> LENGTH: 21
<212> TYPE: DNA
<213> ORGANISM: Homo sapiens

<400> SEQUENCE: 4
ctgcagtgtg ggtttcgggc a                                                  21

<210> SEQ ID NO 5
<211> LENGTH: 25
<212> TYPE: DNA
<213> ORGANISM: Homo sapiens

<400> SEQUENCE: 5
aggagttgtc aaggcagaga agaga                                              25

<210> SEQ ID NO 6
<211> LENGTH: 21
<212> TYPE: DNA
<213> ORGANISM: Homo sapiens

<400> SEQUENCE: 6
gccgccgcga ttgttgtgat t                                                  21

<210> SEQ ID NO 7
<211> LENGTH: 26
<212> TYPE: DNA
<213> ORGANISM: Homo sapiens

<400> SEQUENCE: 7
agtcccaaag gcaaacaacc cacttc                                             26
```

```
<210> SEQ ID NO 8
<211> LENGTH: 27
<212> TYPE: DNA
<213> ORGANISM: Homo sapiens

<400> SEQUENCE: 8
tgctggaggc tgaggtattt ctgtctc                                        27

<210> SEQ ID NO 9
<211> LENGTH: 26
<212> TYPE: DNA
<213> ORGANISM: Homo sapiens

<400> SEQUENCE: 9
tcgcaactat acccagaaca tagaca                                         26

<210> SEQ ID NO 10
<211> LENGTH: 22
<212> TYPE: DNA
<213> ORGANISM: Homo sapiens

<400> SEQUENCE: 10
ctgttgcaaa ggaaccatga ca                                             22

<210> SEQ ID NO 11
<211> LENGTH: 21
<212> TYPE: DNA
<213> ORGANISM: Homo sapiens

<400> SEQUENCE: 11
gcagaagccg agttcaacat c                                              21

<210> SEQ ID NO 12
<211> LENGTH: 21
<212> TYPE: DNA
<213> ORGANISM: Homo sapiens

<400> SEQUENCE: 12
ccttaatgtc acgcacgatt t                                              21

<210> SEQ ID NO 13
<211> LENGTH: 21
<212> TYPE: DNA
<213> ORGANISM: Homo sapiens

<400> SEQUENCE: 13
atggaggagc cgcagtcaga t                                              21

<210> SEQ ID NO 14
<211> LENGTH: 22
<212> TYPE: DNA
<213> ORGANISM: Homo sapiens

<400> SEQUENCE: 14
gcagcgcctc acaacctccg tc                                             22

<210> SEQ ID NO 15
<211> LENGTH: 20
<212> TYPE: DNA
<213> ORGANISM: Homo sapiens

<400> SEQUENCE: 15
ctttccagtg caaccagtgt                                                20
```

```
<210> SEQ ID NO 16
<211> LENGTH: 20
<212> TYPE: DNA
<213> ORGANISM: Homo sapiens

<400> SEQUENCE: 16
gtgaggctta ccaacggagt                                               20

<210> SEQ ID NO 17
<211> LENGTH: 21
<212> TYPE: DNA
<213> ORGANISM: Homo sapiens

<400> SEQUENCE: 17
acacgtgtgc actccaccac t                                             21

<210> SEQ ID NO 18
<211> LENGTH: 21
<212> TYPE: DNA
<213> ORGANISM: Homo sapiens

<400> SEQUENCE: 18
tgaaatccgt ggcctggagg a                                             21

<210> SEQ ID NO 19
<211> LENGTH: 20
<212> TYPE: DNA
<213> ORGANISM: Homo sapiens

<400> SEQUENCE: 19
aagagaggtg gggaggtgat                                               20

<210> SEQ ID NO 20
<211> LENGTH: 19
<212> TYPE: DNA
<213> ORGANISM: Homo sapiens

<400> SEQUENCE: 20
cagcagcaac aagcaggac                                                19

<210> SEQ ID NO 21
<211> LENGTH: 20
<212> TYPE: DNA
<213> ORGANISM: Homo sapiens

<400> SEQUENCE: 21
gatgccgtcg ggtgaatttg                                               20

<210> SEQ ID NO 22
<211> LENGTH: 21
<212> TYPE: DNA
<213> ORGANISM: Homo sapiens

<400> SEQUENCE: 22
tctctatggt taccgcctcc t                                             21

<210> SEQ ID NO 23
<211> LENGTH: 25
<212> TYPE: DNA
<213> ORGANISM: Homo sapiens

<400> SEQUENCE: 23
ttaataaggg aaattttatt gtttt                                         25
```

<210> SEQ ID NO 24
<211> LENGTH: 25
<212> TYPE: DNA
<213> ORGANISM: Homo sapiens

<400> SEQUENCE: 24
ctaacctcaa taccccctaa tattc                                      25

<210> SEQ ID NO 25
<211> LENGTH: 21
<212> TYPE: DNA
<213> ORGANISM: Homo sapiens

<400> SEQUENCE: 25
ctaaggctat cgatagctat c                                          21

<210> SEQ ID NO 26
<211> LENGTH: 21
<212> TYPE: DNA
<213> ORGANISM: Homo sapiens

<400> SEQUENCE: 26
aacggagtta cgatcgatcg a                                          21

<210> SEQ ID NO 27
<211> LENGTH: 20
<212> TYPE: DNA
<213> ORGANISM: Homo sapiens

<400> SEQUENCE: 27
ccatcgatcg accaaccagt                                            20

<210> SEQ ID NO 28
<211> LENGTH: 21
<212> TYPE: DNA
<213> ORGANISM: Homo sapiens

<400> SEQUENCE: 28
ggtttccgat cgctagctag c                                          21

<210> SEQ ID NO 29
<211> LENGTH: 19
<212> TYPE: DNA
<213> ORGANISM: Homo sapiens

<400> SEQUENCE: 29
ttcgatcgct agctcggga                                             19

<210> SEQ ID NO 30
<211> LENGTH: 20
<212> TYPE: DNA
<213> ORGANISM: Homo sapiens

<400> SEQUENCE: 30
tttcccggaa attcggattc                                            20

<210> SEQ ID NO 31
<211> LENGTH: 20
<212> TYPE: DNA
<213> ORGANISM: Homo sapiens

<400> SEQUENCE: 31

```
ttccccggag ccacgattac                                              20

<210> SEQ ID NO 32
<211> LENGTH: 19
<212> TYPE: DNA
<213> ORGANISM: Homo sapiens

<400> SEQUENCE: 32
taagcgctcc gagctagct                                               19

<210> SEQ ID NO 33
<211> LENGTH: 19
<212> TYPE: DNA
<213> ORGANISM: Homo sapiens

<400> SEQUENCE: 33
atggccctta ggctaccga                                               19

<210> SEQ ID NO 34
<211> LENGTH: 19
<212> TYPE: DNA
<213> ORGANISM: Homo sapiens

<400> SEQUENCE: 34
ccgggctaga tatcgctag                                               19

<210> SEQ ID NO 35
<211> LENGTH: 21
<212> TYPE: DNA
<213> ORGANISM: Homo sapiens

<400> SEQUENCE: 35
ccagtgtaat tcgctagcta g                                            21

<210> SEQ ID NO 36
<211> LENGTH: 21
<212> TYPE: DNA
<213> ORGANISM: Homo sapiens

<400> SEQUENCE: 36
aacggagttc gatcgatata t                                            21

<210> SEQ ID NO 37
<211> LENGTH: 21
<212> TYPE: DNA
<213> ORGANISM: Homo sapiens

<400> SEQUENCE: 37
ttcgagtggc ccactcgaac c                                            21

<210> SEQ ID NO 38
<211> LENGTH: 21
<212> TYPE: DNA
<213> ORGANISM: Homo sapiens

<400> SEQUENCE: 38
ttaccaatcg atcgacacta a                                            21
```

MODIFIED RESVERATROL COMPOSITION AND USE THEREOF

CROSS-REFERENCE TO RELATED APPLICATIONS AND PRIORITY

The present application claims priority from a U.S. provisional patent application No. 62/380,986 filed on 29 Aug. 2016, a U.S. provisional patent application No. 62/381,009 filed on 29 Aug. 2016, a U.S. provisional patent application 62/445,255 filed on 12 Jan. 2017, a U.S. provisional patent application No. 62/381,000 filed on 29 Aug. 2016, a U.S. provisional patent application No. 62/445,257 filed on 12 Jan. 2017, an Indian Provisional Application 201721019179 filed on 31 May 2017 and a PCT application PCT/IB2017/050767 filed on 11 Feb. 2017, the entirety of which is hereby incorporated by reference.

TECHNICAL FIELD

Invention generally relates field of medicine, and more particularly medicinal or therapeutic use of a modified resveratrol composition, for regulating gene expression in order to improve insulin sensitivity, Dehydroepiandrosterone (DHEA) levels and cell longevity, to activate very small embryonic like stem cells, to aid in in-vitro fertilization techniques, for treatment of various types of cancers, for regulating the gene expression in order to achieve beneficial effects in cancer treatment and other uses affecting health parameters of a mammal.

BACKGROUND

Modern medicine was expected to undergo a sea-change by the discovery of resveratrol (3,5,4'-trihydroxy-trans-stilbene), a natural anti-oxidant molecule present in skins and peels of grapes, mulberries, groundnuts and red wine etc. that delays aging by acting on multiple organs by improving DNA repair & protein function, cellular detoxification and energy production. Studies done in animal models suggest that it prevents neuro-degeneration, ovarian function, infertility, muscular dystrophy, increased longevity, diabetes and cancer. Based on the results that resveratrol directly activated $NAD^+$ dependent protein deacetylase SIRT1 thereby regulating mitochondrial function. Resveratrol has an ability to directly activate $NAD^+$ dependent protein deacetylase SIRT1 thereby regulating mitochondrial function. Despite the various controversies it is mired in, resveratrol is a good anti-aging molecule and activates sirtuins. Glaxo Smith Kline in 2008 invested $720 million to buy Sirtris Pharmaceuticals Inc. co-founded in 2004 by David Sinclair, a scientist from Harvard Medical School, USA. However, the field became mired by controversies and the company was shut down five years later since the results published by Sinclair's group were doubted on technical grounds. However, recently data has generated further evidence to show that indeed SIRT1 is activated by resveratrol in vitro on substrate without a fluorescent tag. Resveratrol is a good anti-aging molecule and activates sirtuins but major problems associated with bringing it to the market include (i) it exhibits effects on multiple targets (ii) basic mechanism of action is not well understood and (iii) issues with bioavailability. Most importantly, FDA is keen to know defined mechanism of a molecule on a specific target prior to allowing it to be marketed as a drug.

Resveratrol molecule is a very potent natural biological polyphenol that has antioxidative effect on the cellular processes. It has a unique ability to modulate multiple cellular targets and is therefore suitable for the prevention and treatment of wide variety of diseases. One or more beneficial health effects of resveratrol attract interest of patients suffering from wide spectrum of medical and health issues.

One of the possible areas of interest in this regard are cardiovascular diseases and related ailments. In today's times, Cardiovascular diseases are the leading cause of death globally. Along with a few nutraceutical compositions, there are few surgical treatments and allopathic drug treatments available to maintain the lipid profile level in the blood plasma, however, they may have some side effects and fail to provide long-term beneficial effect. Hence, there is a need of peculiar nutraceutical medication which efficiently maintain the lipid profile level in the blood plasma by providing synchronized support for other medicinal treatments.

Another potential area of interest in this regard are diabetes, insulin resistance, metabolic syndrome and related ailments. Diabetes progression starts with an underlined condition called insulin resistance. Insulin resistance is a condition wherein body produces insulin but fails to utilize it effectively. This leads to glucose built up in the blood rather than being absorbed by the cells. Insulin resistance if remains untreated can prepare the foundation for Type 2 diabetes or prediabetes. Insulin resistance increase is said to be an ageing phenomenon triggered by silencing and activation of the genes. Nicotinamide adenine dinucleotide phosphate (NADPH), Glyceraldehyde 3-phosphate dehydrogenase (GADPH), TXNIP (Thioredoxin-interacting protein encoder), SIRT1 (silent mating type information regulation 2 homolog—sirtuin), 2,4 Dienoyl-CoA reductase (DECR) genes have a potential role in insulin resistance. Diabetes, whether or not preceded by insulin resistance is treated with insulin. Prolonged use of insulin has a variety of side effects on an individual, these primarily include cell ageing; loss of sight and hearing capacity, loss of nervous function, renal function and at times amputation of the lower limbs. These side effects can be lessened by targeting NFKB1 (Nuclear factor NF-kappa-B p105 subunit encoder), NFKB2 (Nuclear factor NF-kappa-B p100 subunit encoder) and TP53 (gene which encodes for p53 protein) genes. Targeting the genes to regulate these levels is a quicker and effective way to treat diseases. Whereas, any allopathy drug takes at least a month to stabilize the levels and bring them into ideal range later on.

Yet another potential area of interest in this regard is artificial reproductive technology (ART) which depends of optimum levels of crucial hormones like anti-mullerine hormone (AMH), estradiol among others. Though the ART provide promising solution to the infertility, the success rate of IVF is not ideal. Low levels of AMH and Estradiol can affect the oocyte quality and quantity. Hence, the formulation with less adverse side-effect is required for giving a better yield of healthy oocytes for ART treatments and to ensure successful implantation of the transferred embryo later on. Such formulation is desirable to prevent probable future risks associated with artificially induced superovulation.

Still another area of interest in this regard is treatment for muscular dystrophy. Muscular dystrophy is a group of muscle diseases characterized by progressive muscle weakness and degeneration. Muscular Dystrophy is caused due to mutations in genes that are involved in making muscle proteins. The Duchenne muscular dystrophy (DMD) is the most common and severe form of X-linked Muscular dystrophy caused by mutation in the gene that encodes dystrophin. Currently, the only approved treatment for patients with DMD are corticosteroids, which improve muscle weakness and delay disease progression. Nonetheless, the use of corticosteroids is linked with numerous side effects, such as osteoporosis, metabolic diseases and development of gastric ulcers and resveratrol formulation for tackling muscular dystrophy is need of the day.

Still another area of interest in this regard is activation of stem cell pathway which can aid in regeneration of tissue and for anti-ageing. Resveratrol is known to stimulate very small embryonic like stem cells VSELs help their differentiation into various cell types in peripheral blood, to activate the hematopoietic system by promoting self-renewal of pluripotent VSELs and their differentiation into Hematopoietic stem cells (HSC), Mesenchymal Stem cells (MSC) and Endothelial Progenitor Cells (EPC).

Even though resveratrol possesses great potential and is used as a part of many medicines and dietary supplements, the utilization of resveratrol molecule is currently limited due to its unfavorable pharmacokinetic properties. Resveratrol exhibits maximum activity in its free, unreacted form. Being a phenolic compound resveratrol gets rapidly metabolized and eliminated from body, exhibiting low bioavailability in the body when administered orally, which is one of the major limitations. The resveratrol that remains in the bloodstream exist in conjugated form and thus the important antioxidant effect is neutralized. Effectiveness of resveratrol in vivo has been limited by its low bioavailability in the free unreacted form. Various factors such as low concentration of free resveratrol, low stability of free resveratrol in administered formulation, low absorption of free and unreacted resveratrol, low stability of free resveratrol leading to its conversion into less active forms and sulfonation and glucuronidation of resveratrol in the free unreacted form.

In the light of foregoing problems, there exists a need for such a resveratrol formulation which is potent in small doses, highly bioavailable and has increased half-life for treatment of a mammal with predetermined dosage for a predetermined period, and application thereof to the various ailments and disease conditions afflicting the mammalian body.

The invention described herein below attempts to address the technical problems identified in the preceding paragraphs.

SUMMARY

This summary is provided to introduce aspects related to. use of a modified resveratrol composition, for regulating gene expression in order to improve insulin sensitivity, Dehydroepiandrosterone (DHEA) levels and cell longevity, to activate very small embryonic like stem cells, to aid in in-vitro fertilization techniques, for treatment of various types of cancers, for regulating the gene expression in order to achieve beneficial effects in cancer treatment and other uses affecting health parameters of a mammal. It is to be understood that this application is not limited to the particular process steps described in particular order, as there can be multiple possible embodiments which are not expressly illustrated in the present disclosure. The terminology used in the summary or description is for the purpose of describing the particular versions or embodiments only, is not intended to identify essential features of the claimed subject matter nor is it intended for use in determining or limiting the scope of the claimed subject matter.

In accordance with an aspect of the present subject matter, a resveratrol delivery system comprising a modified resveratrol composition, wherein, said modified resveratrol composition may comprise colloidally stable resveratrol nanoparticles having tree fat coating, characterized in that said modified resveratrol composition administered to a mammal suffering from insulin resistance, metabolic syndrome, aging, apoptosis, inflammation, stress resistance, cancer, cardiovascular disease, muscular dystrophy, low fertility rates or any combination thereof in a predetermined therapeutically effective amount,
  a) upregulates expression of genes coding for 2,4 Dienoyl-CoA reductase (DECR), Nicotinamide adenine dinucleotide phosphate (NADPH) silent information regulator 1 (SIRT 1), silent information regulator 6 (SIRT 6), apolipoprotein E (APOE), lipoprotein lipase (LPL), Anti Müllerian hormone (AMH) and p53 protein in mammals, and
  b) downregulates expression of genes coding for Nuclear factor NF-kappa-B p105 subunit (NFkB1), Nuclear factor of kappa light polypeptide gene enhancer in B-cells 2 (NFkB2) and Thioredoxin-interacting protein (TXINP) in mammals,
  further characterized in that, said modified resveratrol composition comprises of nanoparticles having a particle size of less than 100 nm with a zeta potential value below −20 mv between a pH range of 2 to 12 having tree fat coating, wherein the nanoparticles are capable of retaining stabilized and unconjugated form of resveratrol in blood plasma at a concentration in a range of 10000 nmoles/liter to 40000 nmoles/liter, with half-life of at least 3 hours when administered orally in mammalian body, is disclosed.

In accordance with another aspect of the present subject matter, a modified resveratrol composition, comprising conjugation stable resveratrol nanoparticles, wherein said colloidally stable resveratrol nanoparticles are synthesized by a process comprising the steps of:
  a) selecting the matured kernels that contain resveratrol;
  b) germinating the matured kernels by soaking them in a nutrient medium for prescribed period of time, optimally up to 11 days by maintaining predefined temperature and a varying magnetic strength to enhance the resveratrol content in the kernels;
  c) drying the sprouted kernels for at least 1 day, wherein critical cycles of temperatures are maintained;
  d) crushing the dried kernels and obtaining purified resveratrol molecules for preparing a formulation having colloidally stable resveratrol nanoparticles;
  e) coating resveratrol molecules with tree fat, to form colloidally stable resveratrol nanoparticle by incubating the resveratrol nanoparticle with the tree fat under constant mechanical stirring, for predefined period of time, optimally up to 24 hours;
  wherein up to 90% coated nanoparticles having a particle size less than 100 nm, characterize in that the nanoparticles are capable of retaining stabilized and unconjugated form of resveratrol at a concentration in a range of 10000 nmoles/liter to up to 40000 nmoles/liter, with half-life of at least 3 hours when administered in mammalian body, is disclosed.

In accordance with an aspect of the present subject matter, a modified resveratrol composition which comprises resveratrol from natural sources, preferably peanut skin and wherein said tree fat is obtained preferably from Jackfruit tree, is disclosed. Hereinafter, Jackfruit tree is interchangeably referred as Jackfruit plant.

In accordance with an aspect of the present subject matter, a modified resveratrol composition regulating the gene expression in order to regulate blood profile, kidney profile, liver profile, and insulin levels for improving insulin sensitivity, Dehydroepiandrosterone (DHEA) levels and cell longevity in the human beings is disclosed.

In accordance with another aspect of the present subject matter, a modified resveratrol composition which activates of S447X gene to modulate the HDL, VLDL and TG (Triglyceride levels) levels and activates Apolipoprotein E (APOE) gene to modulate the LDL level, is disclosed.

In accordance with another aspect of the present subject matter, a modified resveratrol composition for increasing yield of healthy oocyte and facilitating the embryo implantation to the uterine wall by maintaining the AMH and Estradiol hormones respectively with the help of resveratrol is disclosed.

In accordance with another aspect of the present subject matter, a modified resveratrol composition regulates expression of DHEA proteins and p53 protein in order to achieve beneficial effect in cancer treatment is disclosed.

In accordance with another aspect of the present subject matter, process of formulation of a modified resveratrol composition with increased bioavailability and increased half-life and optionally, additionally containing a second active ingredient niacin or vitamin B3, is disclosed.

In accordance with another aspect of the present subject matter, the modified resveratrol composition which has very high bioavailability and half-life and which is alternatively abbreviated as eXtremely Active Resveratrol (XAR) molecule, is disclosed.

In accordance with another aspect of the present subject matter effects of a modified resveratrol composition on activation of very small embryonic like stem cells (VSEL stem cells), and subsequently on expression of genes coding for marker proteins like Oct4, Oct 4A, Nanog, Sox 2, Ikaros, CD90, CD14 as well as genes coding for regulators of insulin resistance and cancer like SIRT, NAMPT, Tp53, is disclosed.

BRIEF DESCRIPTION OF FIGURES

FIG. 1 illustrates SEM analysis of Tree fat coated Resveratrol nanoparticles

FIG. 3 illustrates HR-TEM analysis of Tree fat coated Resveratrol nanoparticles

FIG. 4 illustrates Zeta potential analysis of Resveratrol nanoparticles coated with tree fat FIG. 5 illustrates Bioavailability and half-life of orally administered resveratrol

FIG. 10 illustrates effect of modified resveratrol composition induced activation of VSEL stem cells on the lipid profile, cholesterol levels, triglyceride levels, insulin levels of experimental subjects

DETAILED DESCRIPTION

Figure 2:
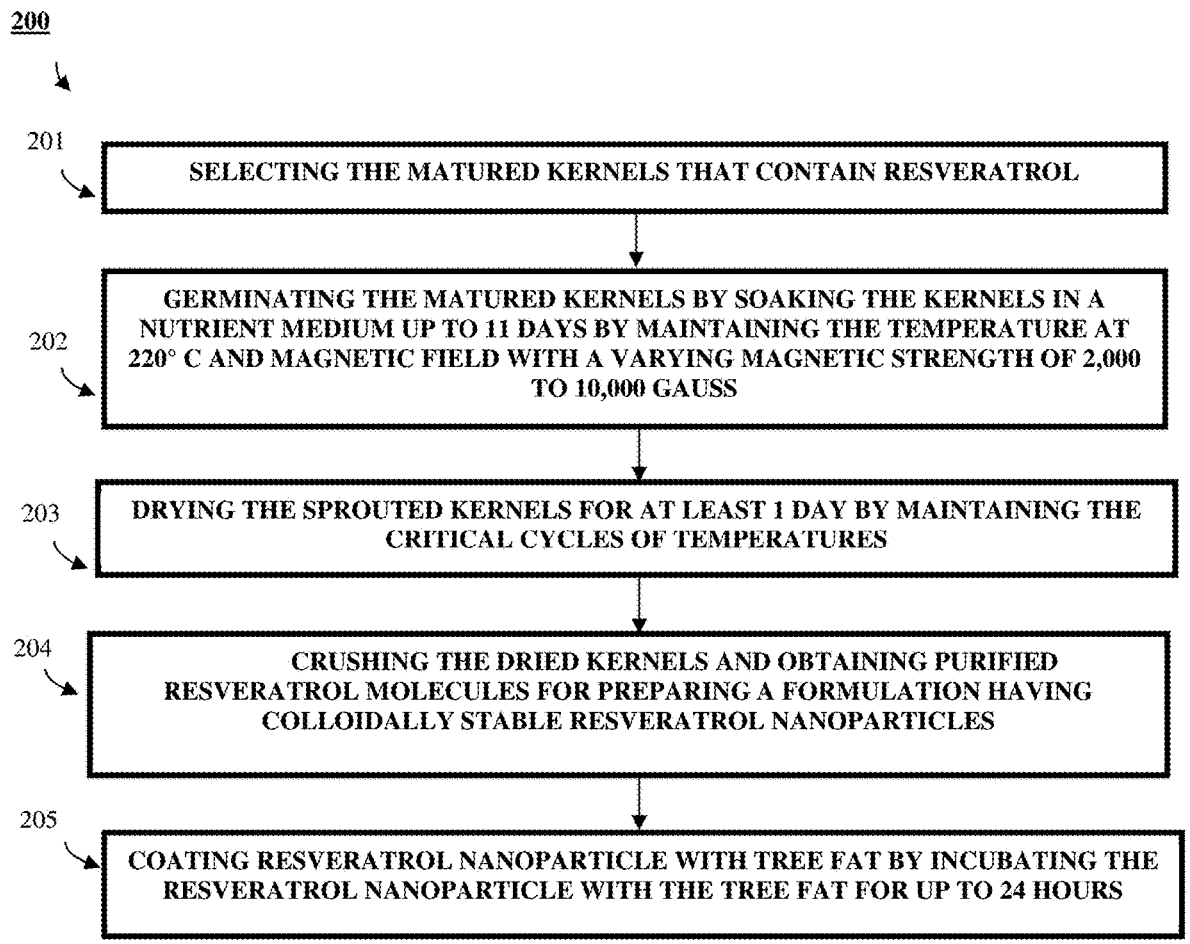
FIG. 2 illustrates process for obtaining modified resveratrol composition.

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that, the singular forms "a," "an," and "the" include plural references unless the context clearly dictates otherwise.

The exemplary embodiments described herein and claimed hereafter may be suitably practiced in the absence of any recited feature, element or step that is, or is not, specifically disclosed herein. For instance, references in this written description to "one embodiment," "an embodiment," "an example embodiment," and the like, indicate that the embodiment described can include a particular feature, structure, or characteristic, but every embodiment may not necessarily include the particular feature, structure, or characteristic. The disclosed embodiments are merely exemplary of various forms or combinations. Moreover, such phrases are not necessarily referring to some embodiment. Further, when a particular feature, structure, or characteristic is described in connection with an embodiment, it is submitted that it is within the knowledge of one of ordinary skill in the art to affect such feature, structure, or characteristic in connection with other embodiments whether or not explicitly described.

No or terminology in this application should be construed as indicating any non-claimed element as essential or critical. The use of any and all examples, or example language (e.g., "such as") provided herein, is intended merely to better illuminate example embodiments and does not pose a limitation on the scope of the claims appended hereto unless otherwise claimed.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller subranges are also included. The upper and lower limits of these smaller ranges are also included therein, subject to any specifically excluded limit in the stated range. For example, a range of "about 0.1% to about 5%" or "about 0.1% to 5%" may be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

System(s) for delivering colloidally stable resveratrol nanoparticles and process(es) for synthetization the same is described. In recent years, the use of resveratrol as an antioxidant to improve health as well as mental and physical energy has greatly increased. Further, resveratrol is unique in its ability to modulate multiple cellular targets and is therefore, suitable for the prevention and treatment of wide variety of ailments. Resveratrol exerts a plethora of health benefits through many different mechanisms of action. Insulin resistance, cell longevity and many cell regulatory pathways are regulated by various gene products of TP53, SIRT1, GADPH, NADPH, TXNIP, DECR, NF-KB1 and NF-KB2 genes. These are required to regulate Blood profile, kidney profile, liver profile, and insulin levels as prescribed in the ideal range of normal values. Resveratrol when made electrolytically compatible may enter the nucleus of the cell and alter gene expression, in one aspect of the present invention the role of resveratrol in up/down regulation of genes another aspect affects the expression of other proteins, hormones, transcription factors etc. Some of the functions of the genes proteins, hormones, transcription factors have been enlisted below:

GADPH—Glyceraldehyde 3-phosphate dehydrogenase (abbreviated as GAPDH or less commonly as G3PDH) is an enzyme that catalyzes the sixth step of glycolysis and thus serves to break down glucose for energy and carbon molecules.

NADPH—Nicotinamide adenine dinucleotide phosphate (NADPH) promotes nitric oxide and glutathione production. Deficiency of glutathione can cause hemolysis under oxidative stress. Nitric oxide acts as a vasodilator. Thus, the crucial role of NADPH to protect blood vessels from damage caused by oxidative stress and their accumulation thereof. In patients with diabetes mellitus if NADPH is oxidized to NADP+ in the presence of high sugar levels can cause damage to the retina.

SirT1—SirT1 is a silent information regulator 1(SIRT1) gene which influence many cellular processes like aging, apoptosis, inflammation and stress resistance.

SirT6—SIRT6 is disrupted in cancer cell lines of the pancreas, stomach, lung, digestive tract, liver, ovary, breast, urinary tract, prostate, biliary tract, esophagus, skin, bone and endometrium with locus deletion in 35% of >1000 cancer cell lines. SIRT6 over-expression resulted in apoptosis of cervical carcinoma, fibrosarcoma, primary and metastatic breast tumor cell lines with no effect on non-transformed cell lines.

TXNIP—Thioredoxin-interacting protein in humans is encoded by the TXNIP gene. TXNIP is involved in the initiation of this destructive process of ER stress, unfolded protein, inflammation and cell death. A protein known as IRE 1 induces TXNIP causing Il-1 production and inflammation. Acts as a suppressor of tumour cell growth DECR 1—2,4 Dienoyl-CoA reductase also known as DECR1 is a protein which in humans is encoded by the DECR1 gene. It is an accessory enzyme which participates in beta oxidation and metabolism of polyunsaturated fatty enoyl-CoA esters. Thus, this gene serves as an ideal therapeutic target for treating non-insulin dependent diabetes mellitus (NIDDM), which causes hyperglycemia due to increased fatty acid oxidation.

TP53—TP53 is a gene which encodes for p53 is known as tumor protein regulating cell cycle and causing tumor suppression. TP 53 has a role of conserving cellular stability by preventing genome mutation. Resveratrol is a promising agent for the prevention of cancer. Our study shows that resveratrol suppresses tumor promoter-induced cell transformation and markedly induced apoptosis by expression of p53 protein.

NF-KB1—Nuclear factor NF-kappa-B p105 subunit is a protein that in humans is encoded by the NFKB1 gene. NF-KB1 is responsible for TNF induced endothelial activation and vascular inflammation play a critical role in vascular aging and atherogenesis.

NF-KB2—Nuclear factor of kappa light polypeptide gene enhancer in B-cells 2. This gene encodes a subunit of the transcription factor complex nuclear factor-kappa-B (NFkB) which plays an important role in activation of the genes responsible for inflammation and other immune responses.

Apolipoprotein E (ApoE)—APOE gene encodes apolipoprotein E (APOE) which is a class of apolipoprotein found in the lipid profile such as chylomicron and Intermediate-density lipoprotein (IDLs). ApoE is an essential part of lipoprotein metabolism. Apolipoprotein E is a blood plasma protein responsible for the transport of lipids and cholesterol by way of interaction with the low-density lipoprotein (LDL) receptor. APOE is essential for the normal catabolism of triglyceride-rich lipoprotein.

S447X gene—S447X gene encodes for lipoprotein lipase (LPL) which has an essential role in lipid homeostasis and energy metabolism.

Dehydroepiandrosterone (DHEA)—DHEA is produced by the adrenal glands and used by the body for estrogen and testosterone production. Blood levels of DHEA rise until they peak in the third decade of life, then rapidly decline.

Oct4 (octamer-binding transcription factor 4)—Oct 4 IS also known as 20 Aggeliki (POU domain, class 5, transcription factor 1) is frequently used as a marker for undifferentiated cells. Oct-4 expression must be closely regulated; too much or too little will cause differentiation of the cells. Transcription, alternative splicing, and alternative translation of Oct 4 leads to the synthesis of the active, nuclear localized Oct4a which is a core component of the regulatory network of pluripotent cells, and by 25 itself can reprogram neural stem cells into pluripotent cells in mice and humans.

NANOG—NANOG is believed to function in conjunction with other factors such as Oct4 and Sox2 to form an embryonic stem cell identity and Nanog expression has been reported in human neoplasms, including germ cell tumors, breast carcinoma, and osteosarcoma.

SRY (sex determining region Y)-box 2—Sox2, is a transcription factor that is essential for maintaining self-renewal, or pluripotency, of undifferentiated embryonic stem cells. Sox2 has a critical role in maintenance of embryonic and neural stem cells.

Anti Müllerian hormone (AMH)—The ovarian reserve is a capacity of the ovary to provide oocytes that are capable of fertilization resulting in a healthy and successful pregnancy. Thus, in IVF treatment detection of relative size of the ovarian reserve has significance importance. The Anti Müllerian hormone which is known as AMH serves as molecular biomarker for detection of ovarian reserve. AMH is a hormone which is found to be secreted by the granulosa cells of ovarian follicles in females. The number of oocyte in the ovarian reserve can be used to predict success rate of pregnancy and age of menopause. Thus, the use of AMH as a biomarker has proven to be helpful to strategize and take a decision to opt for cryopreservation of oocyte or egg freezing especially in cancer patients undergoing chemotherapy AMH is not only important as a strong molecular biomarker of a woman's ovarian reserve but also it plays an important role in increasing the oocyte yield. In order to collect the sufficient eggs for the IVF process, the woman needs to undergo an ovarian stimulation. Women with higher AMH values will tend to have a good response to ovarian stimulation and which leads to more eggs retrieval. Thus, higher number of oocytes improves the success rate, as out of multiple oocytes at least one high quality oocyte can be available for healthy embryo development. Hence it can be said that the level of AMH is important to increase the probability of success in IVF treatment of those cases in which recovery of multiple healthy oocytes is possible.

Estradiol—Estradiol is yet another important hormone which is crucial in the successful pregnancy. Estradiol, is a primary female sex hormone and produced especially within the follicles of the female ovaries. Estradiol appears necessary to maintain oocytes in the ovary and also reflects primarily the activity of the ovaries. Furthermore, estrogen monitoring during fertility therapy assesses follicular growth and is useful in monitoring the treatment. Estradiol plays an imperative role in determining the window of opportunity for an embryo to attach itself to the uterine wall and for further development.

Referring to FIG. 1, in yet another embodiment, the resveratrol nanoparticle may form a colloid post surface coating with tree fat as observed in SEM analysis. Resveratrol molecule in its colloidal and surface modified form inhibit its glucuronidation and sulfonation, thus slows down or inhibits its hepatic metabolism. Referring now to FIG. 1 (A) & (B), resveratrol nanoparticles having tree fat coating, wherein up to 90% nanoparticles having a particle size less than 100 nm are illustrated, in accordance with an embodiment of the present subject matter. Although the present subject matter is explained considering that the resveratrol is derived from natural source by the process explained in the disclosure, it may be understood that resveratrol molecules derived from natural sources by other processes than the process explained in the disclosure may also be implemented. The resveratrol nanoparticles are capable of retaining stabilized and unconjugated form of resveratrol at a concentration in a range of 10000 nmoles/liter to 40000 nmoles/liter, with half-life of at least 3 hours when administered in mammalian body. The resveratrol is derived from natural source, preferably peanut kernels and such tree fat is obtained preferably from Jackfruit.

Referring now to FIG. 2, the process 200 for synthesizing colloidally stable resveratrol nanoparticles, wherein up to 90% nanoparticles having a particle size less than 100 nm characterize in that the nanoparticles are capable of retaining stabilized and unconjugated form of resveratrol at a concentration in a range of 10000 nmoles/liter to up to 40000 nmoles/liter, with half-life of at least 3 hours when administered in mammalian body, is illustrated in accordance with an embodiment of the present subject matter.

The order in which the process 200 is described is not intended to be construed as a limitation, and any number of the described method blocks can be combined in any order to implement the process 200 or alternate process. Additionally, individual blocks may be deleted from the process 200 without departing from the spirit and scope of the subject matter described herein. Furthermore, the process can be implemented using any suitable natural source of resveratrol or combination thereof. However, for ease of explanation, in the embodiments described below, the process 200 may be considered to be implemented in the above described resveratrol delivery system.

At block 201, matured kernels that contain resveratrol preferably, peanuts are selected.

At block 202, matured kernels are subjected to germination process by soaking the kernels in a mineral nutrient medium for optimally up to 11 days by maintaining the temperature at 220° C. During the sprouting phase, while kernels are placed in the mineral nutrient medium, a magnetic field is applied to the medium by placing them in a magnetic zone with a varying magnetic strength of 2,000 to 10,000 gauss.

At block 203, the sprouted kernels are harvested and dried for at least 1 day, in a mechanized auto-control dryer by maintaining the critical cycles of temperatures.

At block 204, dried sprouted kernels are crushed and purified resveratrol molecules are obtained for preparing a formulation having colloidally stable resveratrol nanoparticle. In one embodiment, the resveratrol nanoparticles are purified from crushed kernels by adding the crushed kernels in Phosphate buffered saline solution and the mixture is centrifuged at 10,000-12,000 rpm for 5-10 minutes, resulting in the pellet formation which contains resveratrol nanoparticles.

At block 205, resveratrol nanoparticles are coated with tree fat by incubating the resveratrol nanoparticles with the tree fat, under constant mechanical stirring at 400-800 rpm, for up optimally to 24 hours. In one embodiment, the ratio of the tree fat to resveratrol is 3:1 to 5:1 in the colloidally stable resveratrol nanoparticles. In one implementation, such tree fat is obtained preferably from Jackfruit. In one embodiment, at block 205, resveratrol nanoparticles are coated with a jackfruit tree fat coating.

In yet another embodiment, the process 200 as disclosed in FIG. 2, enhances the resveratrol content in the kernels. As the kernels are germinated in the mineral nutrient medium at 220° C. for optimally up to 11 days, it enhances the resveratrol content in the kernels significantly, within the period of germination. Resveratrol is an antioxidant, synthesized by kernels in response to biotic or abiotic stress or pathogen attack; hence when the kernels are subjected to extreme temperature (abiotic stress) and humidity in presence of mineral rich medium, the kernels up-regulate resveratrol production.

In one embodiment, during the sprouting phase while kernels are placed in the mineral nutrient medium, a magnetic field is applied to the medium by placing them in a magnetic zone with a varying magnetic strength of 2,000 to 10,000 gauss which leads to rearrangement of mineral ions inside the kernels.

In yet another embodiment, magnetic field acts as catalyst and the minerals act as reducing agent which leads dot the formation of resveratrol nanoparticle. This resveratrol nanoparticle can enter the nucleus and can control the on/off cycle of genes.

In one preferred embodiment, the kernels are peanut kernels. Out of all natural sources, Peanut kernel is one of the widely available, potent and more consistent source of resveratrol, which contains ample amount of resveratrol with potent antioxidant properties.

Referring now to FIG. 3, each resveratrol nanoparticle coated with tree fat is illustrated. In one implementation, the resveratrol is derived from natural source, preferably peanut kernels and wherein such tree fat is obtained preferably from Jackfruit.

In one embodiment, 4% -90% particles of the colloidally stable resveratrol nanoparticles have a particle size less than 100 nm.

In one embodiment, all resveratrol nanoparticles are uniform in size.

In another embodiment, the ratio of tree fat to resveratrol is 3:1 to 5:1 in the colloidally stable resveratrol nanoparticles.

In another embodiment, each resveratrol nanoparticle comprises up to 1000 molecules of resveratrol.

An electrostatic repulsion is a measure colloidal stability of tree fat coated nanoparticle and is measured in terms of Zeta Potential which is a measure of surface charge of such coated nanoparticle. An absolute zeta potential value in the range of ≥−20 to −30 mv represents stable colloidal nanoparticles that will repel and thereby may not agglomerate. Referring to FIG. 4, the zeta potential of the coated nanoparticles of the current invention is negatively charged. The trend showed that the nanoparticles are charge stabilized at both lower and higher pH. The range of pH is in between 2 to 12. In one embodiment, the resveratrol nanoparticles having tree fat coating are electrostatically stable since an absolute zeta potential value of the resveratrol nanoparticles having tree fat is in the range of ≥−20 to −30 mv between pH 2 to 12.

Referring now to FIG. 5 (A) & (B), in yet one embodiment, resveratrol molecule is delivered in the free, unconjugated form at a concentration in the range of 10000 nmoles/liter to up to 40000 nmoles/liter in the blood plasma. FIG. 5 (A) and (B) describes the mean and maximum pharmacokinetic parameters, for resveratrol and its metabolites (glucuronides, sulphates) based on the plasma levels of healthy individuals following oral administration of colloidally stable resveratrol nanoparticles. The maximum bioavailability and mean bioavailability of unconjugated resveratrol is up to 40,000 nmol/L and 11,234 nmol/L respectively, with a significant half life of at least 3 hours. The concentration of resveratrol conjugates is very low, only 1.3% of the orally administered resveratrol underwent metabolism and resulted in formation of resveratrol conjugates whereas 98.7% of resveratrol is retained in its unconjugated/free form in blood plasma. In one embodiment the coating of tree fat around the resveratrol nanoparticle, stabilizes the resveratrol nanoparticle and avoid its agglomeration at pH between 2-12. Ordinarily the Resveratrol forms conjugates by Sulfonation and glucuronidation in the liver of human body. Such Sulfonation and glucuronidation is prevented when Resveratrol nanoparticle gets coated with tree fat. As a result, the administered resveratrol has enhanced threshold bioavailability and half-life.

Generally, in the bloodstream, resveratrol molecule can be found essentially in three different forms: glucuronide form, sulfate form, or free form. Resveratrol molecule has high metabolic rate which causes production of conjugated sulfates and glucuronides. Once absorbed, resveratrol molecule is rapidly metabolized by conjugation to glucuronic acid and/or sulfate, forming resveratrol molecule glucuronides, sulfates. Glucuronidation eliminate the therapeutic efficacy of resveratrol molecule thereby resulting in the therapeutically low threshold bioavailability of resveratrol molecule. In one embodiment, the resveratrol nanoparticle surface coated with tree fat enables the resveratrol to retain its free/unconjugated form. In one embodiment, the colloidally stable resveratrol nanoparticle due to its nanoparticle form does not undergoes metabolism and remains free in the blood which further gets absorbed at a cellular level. The tree fat coating of resveratrol nanoparticle provides stability to the nano-formulation at pH value between 2-12 in the mammalian body.

The oral bioavailability of resveratrol molecule is negligible due to unwanted and quick metabolism and the consequent formation of various metabolites such as glucuronides sulfates. The glucuronide and sulfate conjugates decrease circulating levels of free resveratrol molecule. Thus, metabolism of resveratrol molecule results in relatively small amounts of free resveratrol molecule in the plasma to be delivered to other tissues. In one embodiment, therapeutically low threshold bioavailability of the resveratrol molecule is increased by administering the resveratrol molecule in its colloidally stable nanoparticle form in mammalian body.

In one embodiment, the half-life of resveratrol molecule is increased. The nano sized resveratrol molecule results in reduced sulfate conjugation and glucuronidation of resveratrol nanoparticle leading to resveratrol molecule's flux across cellular membranes and nucleus and prevents the excretion of the resveratrol molecule hence increases half-life of resveratrol molecule.

In yet another embodiment, the colloidally stable resveratrol nanoparticle avoids conjugation of resveratrol molecule due its smaller size (size less than 100 nm). Nanoparticle with less than 100 nm does not undergoes metabolism. Thus the half-life of resveratrol molecule is increased.

In yet another embodiment, the colloidally stable resveratrol nanoparticles are capable of retaining free unconjugated resveratrol molecule in the blood stream for up to 6 hours. In preferred embodiment, the half-life of colloidally stable resveratrol nanoparticles is at least 3 hours in a human clinical study.

In one embodiment, the tree fat coated resveratrol nanoparticle in the colloidal form is obtained by using the process described in this written description wherein such tree fat is obtained preferably from Jackfruit.

In a preferred embodiment, the mineral nutrient medium used for soaking the kernels is a mixture of minerals, water and growth media which effects a change in dimension of the resveratrol molecule resulting to its reduction in size, in the presence of magnetic field and formation of a complex with mineral ions. In one embodiment, there are about 92 trace minerals which are present in the nutrient media In an embodiment, the invention relates to a nutraceutical composition comprising modified resveratrol composition containing colloidal resveratrol nanoparticles in unconjugated form with high threshold bioavailability and half-life prepared from a specified herbal source. The preferred natural source for obtaining the resveratrol may be peanut kernels. More particularly the invention may relate to a process using germinated peanut kernels which is known to enhance concentration of resveratrol within the peanuts.

In one embodiment, the invention relates to a modified resveratrol composition which is prepared from a specific process for obtaining enhanced concentration of resveratrol wherein the process may comprise, in a first step, selection of matured peanut kernels. In next step, peanut kernels may be subjected to germination process by soaking the peanut kernels in a mineral nutrient medium up to 11 days by maintaining the temperature at 220° C. and during the sprouting magnetic zone maintaining a varying magnetic strength of 2,000 to 10,000 gauss. In the next step the sprouted peanut kernels may be harvested and dried for at least 1 day, in a mechanized auto-control dryer maintaining the critical cycles of temperatures required. In the last step dried sprouted peanut kernels may be crushed to obtain the harvested kernels which are employed to prepare a composition for delivering modified resveratrol molecule in to a mammalian body. Magnetic field also plays an important role in cation uptake capacity and has a positive effect on nutrient uptake. This leads formation of resveratrol nanoparticle. This resveratrol nanoparticle molecule can enter the nucleus and can control the on/off cycle of genes. In the last step, the resveratrol nanoparticle is coated with tree fat by incubating the resveratrol nanoparticle with the tree fat for up 10 to 24 hours in a concentration of tree fat to resveratrol nanoparticle 3:1 to 5:1 to result in an extremely active resveratrol molecule with high bioavailability and increased shelf life. The said resveratrol formulation may be delivered through any of the plurality of means including but not limited to incorporation into capsule, tablet, tonic, gel, powder, ointment etc.

In an exemplary embodiment, the invention relates to a modified resveratrol composition containing colloidal resveratrol in unconjugated form which is prepared from a specific process for obtaining enhanced concentration of resveratrol wherein the process may comprise and additional step of addition of micro quantities of biorelevant formulations of niacin or vitamin B3 to the aforementioned resveratrol formulation which may serve as the additional active ingredient of the present formulation In one embodiment, the invention relates to the use of modified resveratrol composition containing colloidal resveratrol in unconjugated form for activation of stem cells including but not limited to, the very small embryonic like stem cells, hematopoietic stem cell (HSC), mesenchymal stem cells (MSC), Endothelial progenitors cell (EPC) which may further impact various health and anti-ageing related factors including but not limited to sirtuin-activation pathway and p53 tumor suppression pathway. Under steady-state conditions, small amounts of hematopoietic stem cells (HSCs) constantly leave the bone marrow (BM), penetrate the tissues, and return to the BM or peripheral niches via the blood or the lymphatic system. Recently, a population of very small embryonic-like stem cells (VSELs) was identified in murine adult bone marrow. Murine VSELs (muVSELs) are small, nonhematopoietic cells with high nuclear/cytoplasm ratio and unorganized euchromatin and express markers of pluripotent embryonic and primordial germ cells, and the present invention provides for a method and process for isolation of human VSEL stem cells from experimental subjects exposed to a potent modified resveratrol composition as well as analysis of the health and anti-ageing associated parameters.

Over period of time, constant high glucose damages nerves and blood vessels leading to many complications like heart diseases, decreased functionality of the nervous system, renal function etc. These effects are very similar to those of cell ageing and thus regulation of genes responsible for preventing cell ageing can be of assistance. In one embodiment, the modified resveratrol composition containing colloidal resveratrol nanoparticles in unconjugated form reduces the insulin resistance by upregulating NADPH and DECR gene expressions, activates SirT-1 gene to protect body against ageing related ailments, protects death of the beta cells or loss of their function against mitochondria mediated apoptosis by downregulating TXNIP gene, downregulates expression of NFKB1 and NFKB2 genes to protect from cellular damage and upregulates expression of TP53 gene which acts as tumor suppression gene ensuring cell survival.

In yet another embodiment, the modified resveratrol composition containing colloidal resveratrol nanoparticles in unconjugated form may prevent NADPH oxidation and retina damage in diabetic patients, may reduce fasting sugar, post-prandial sugar, fasting insulin, post prandial insulin and HOMA index (Homeostatic Model Assessment index) depicting significantly decreased insulin resistance, may increase Dehydroepiandrosterone (DHEA) level and may regulate renal functions by decreasing serum creatinine, serum uric acid and BUN (Blood Urea Nitrogen) value.

In one embodiment, the modified resveratrol composition containing colloidal resveratrol nanoparticles in unconjugated form may upregulate S447X gene and APOE gene expression which encodes Lipoprotein Lipase protein and Apolipoprotein E and modulates the lipid profile.

In another embodiment, the modified resveratrol composition containing colloidal resveratrol nanoparticles in unconjugated form may reduce TG (Triglyceride) level and very low density lipoprotein (VLDL) levels through the up regulation of S447X gene, may elevate High Density Lipoprotein (HDL) levels through the up regulation of S447X gene, may reduce Low Density Lipoprotein (LDL) levels through the up regulation of APOE gene, may lower total cholesterol level, lowers Cholesterol/HDL ratio.

In one embodiment, the resveratrol is modified to improve therapeutically low threshold bioavailability of the resveratrol molecule which is increased by administering the resveratrol molecule in its rearranged structural form in mammal's body. In another embodiment, such rearranged structural form may form a colloid. Resveratrol molecule in its colloidal and modified structural form inhibit its glucuronidation, thus slows down its metabolism.

In one preferred embodiment modified resveratrol composition containing colloidal resveratrol nanoparticles in unconjugated form may improve efficacy of the IVF treatment by improving oocyte yield and facilitating the embryo implantation to the uterine wall. The resveratrol may act on AMH gene to upregulate its expression and consequently may increase AMH level without any side effects in women undergoing the IVF treatment which causes better survival of the oocytes, increase in yield of healthy oocytes after ovarian stimulation. The resveratrol further may elevate the Estradiol level in the women giving broader window of opportunity for making uterine wall more receptive for an embryo to attach itself to the uterine wall by thickening of endometrial lining specially of transferred embryos in IVF cases and improves fertility outcome.

In one embodiment, the modified resveratrol composition containing colloidal resveratrol nanoparticles in unconjugated form, through different regulatory mechanisms, may induce apoptosis in tumor cells. The mechanisms of resveratrol-induced suppression of cellular proliferation involve the induction of apoptosis through Fas/CD95, mitochondrial and p53 mediated pathways.

In one embodiment, the modified resveratrol composition containing colloidal resveratrol nanoparticles in unconjugated form may have beneficial effects such as enhanced toxicity to cancer cells, chemo-protective activity to healthy cells around the tumor, vigorous to rest of the 70 trillion cells in the whole body. The side effects caused due to chemotherapy such as cramps, joint pain, nausea, indigestion may be reduced by targeting TP53 (gene which encodes for p53 protein) gene.

In yet another embodiment, the modified resveratrol composition containing colloidal resveratrol nanoparticles in unconjugated form may have beneficial effect for all the visceral organs (heart, liver, kidney, pancreas and adrenal gland) simultaneously along with changes in the expression levels of 8 different genes including activation of tumor suppressor—p53 and downregulation of NFκB.

In one embodiment, the modified composition containing colloidal resveratrol nanoparticles in unconjugated form resulted in 40 µM/L of unconjugated bioavailable resveratrol that further potently activated SIRT1 gene along-with positively modulating Serum creatinine kinase levels is disclosed. The serum creatinine levels serve as a supplemental biomarker for evaluating the severity of Muscular Dystrophy and for evaluating the therapeutic impact of the drug. The SIRT1 gene is the central gene responsible for ameliorating the Muscular dystrophy condition along-with imparting resistance to muscle injury and up-regulating the dystrophin levels.

In one embodiment, the invention relates to the activation of stem cells including but not limited to VSEL, HSC, MSC, EPC etc. by a modified composition containing colloidal resveratrol nanoparticles in unconjugated form. The activation of VSEL, HSC, MSC, EPC may be analyzed by quantification of pluripotent markers (Oct-4a, Oct-4, Nanog and Sox2), anti-aging transcripts (Sirt1, NAD, p53), and markers for HSCs (Ikaros), MSCs (CD90) and EPCs (CD14). Oct4 (octamer-binding transcription factor 4) also known as Aggeliki (POU domain, class 5, transcription factor 1) is frequently used as a marker for undifferentiated cells. Oct-4 expression must be closely regulated; too much or too little will cause differentiation of the cells. Transcription, alternative splicing, and alternative translation of Oct 4 leads to the synthesis of the active, nuclear localized Oct4A which is a core component of the regulatory network of pluripotent cells, and by itself can reprogram neural stem cells into pluripotent cells in mice and humans. Nanog is believed to function in conjunction with other factors such as Oct4 and Sox2 to form an embryonic stem cell identity and Nanog expression has been reported in human neoplasms, including germ cell tumors, breast carcinoma, and osteosarcoma. SRY (sex determining region Y)-box 2, also known as Sox2, is a transcription factor that is essential for maintaining self-renewal, or pluripotency, of undifferentiated embryonic stem cells. Sox2 has a critical role in maintenance of embryonic and neural stem cells. Sirtuin 1 is one of the critical genes of the sirtuin family playing a prominent role in the anti-ageing process by downregulation of tumor inducing factors like p53 gene, NFkB as well as stimulating autophagy by preventing acetylation of proteins (via deacetylation) required for autophagy as demonstrated in cultured cells and embryonic and neonatal tissues.

Figure 6:
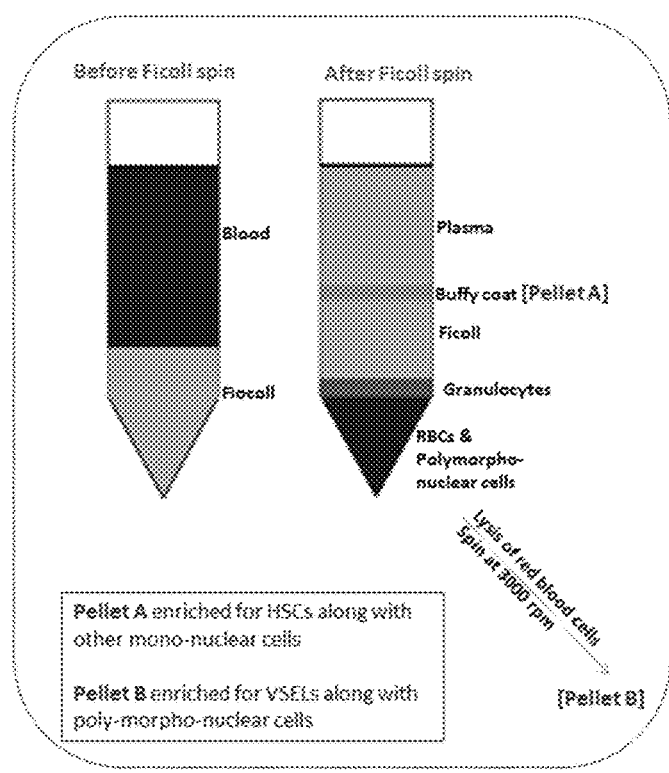
FIG. 6 illustrates the process for purification and isolation of very small embryonic like stem cells as well other stem cells from red blood cells of experimental subjects

In one embodiment, the invention relates to the effect of a modified resveratrol composition containing colloidal resveratrol nanoparticles in unconjugated form wherein the process of analyzing gene expression may be based on the technique of the use of polymerase chain reaction, more specifically with real-time reverse transcription polymerase chain reaction (q-RT PCR). The process of q RT-PCR may further be completed using the standard experimental conditions known in the state of art to assess the transcription levels of the following genes i.e. pluripotent markers (Oct-4a, Oct-4, Nanog and Sox2), anti-aging transcripts (Sirt1, NAD, p53), and markers for HSCs (Ikaros), MSCs (CD90) and EPCs (CD14), as well as genes coding for 2,4 Dienoyl-CoA reductase (DECR), Nicotinamide adenine dinucleotide phosphate (NADPH) or Glyceraldehyde 3-phosphate dehydrogenase (GAPDH), silent information regulator 1 (SIRT 1), silent information regulator 6 (SIRT 6), apolipoprotein E (APOE), lipoprotein lipase (LPL), Anti Müllerian hormone (AMH) and p53 protein, Nuclear factor NF-kappa-B p105 subunit (NFkB1), Nuclear factor of kappa light polypeptide gene enhancer in B-cells 2 (NFkB2) and Thioredoxin-interacting protein (TXINP) in mammals. To carry out the process for e.g. for checking expression of pluripotent marker proteins, RNA is extracted from the experimental sample as outlined in the process described in FIG. 6 in accordance with an aspect of the present invention. The process may include: RNA extraction and cDNA synthesis: Total RNA was isolated from cell pellets in TRiZOL (MP Biomedicals, Irvine, Calif.), according to manufacturer's instructions. First-strand cDNA was synthesized using the Revert Aid First strand cDNA synthesis kit (Thermo scientific, UK) according to the manufacturer's instructions. Briefly, 1 µg of total RNA was incubated with 5× Reaction Buffer and reverse transcriptase mix. The reaction was carried out in Applied Biosystems GeneAmp® thermal cycler 9700 (Applied Bio-systems, USA) as per manufacturer's instructions. The expression levels of various differentiation gene transcripts were estimated by real-time PCR system ABI 7500 (Applied Bio-systems, USA) using Thermo Scientific Maxima SYBR Green/ROX qPCR Master Mix kit (Thermo scientific, UK). The 18 s rRNA was used as housekeeping gene. The primers used in the study are mentioned in Table 1. The amplification conditions were: initial denaturation at 94° C. for 3 minutes followed by 40 cycles comprising of denaturation at 94° C. for 10 seconds, annealing for 20 seconds, and extension at 72° C. for 30 seconds followed by melt curve analysis. The fluorescence emitted was collected during the extension step of each cycle. The homogeneity of the PCR amplicons was verified by running the products on 2% agarose gels and also by studying the melt curve. All PCR amplifications were carried out in duplicate. Mean Ct values generated in each experiment using the 7500 Manager software (Applied Bio-systems, UK) were used to calculate the mRNA expression levels. The fold change was calculated using ΔΔCt method. The relative expression levels of each gene were compared with baseline levels taken as one.

In one embodiment, the invention relates the effect of a modified resveratrol composition containing colloidal resveratrol nanoparticles in unconjugated form induced activation of VSEL stem cells as well other types of stem cells wherein process of analyzing expression of markers may employ the technique of real-time reverse transcription polymerase chain reaction, wherein the said process may comprise the use of specific designed primer sequences for analysis of expression of aforementioned genes, wherein said specified primer sequences may comprise a set of forward primers with Seq. Id. 1, Seq. Id. 3, Seq. Id. 5, Seq. Id. 7, Seq. Id. 9, Seq. Id. 11, Seq. Id. 13, Seq. Id. 15, Seq. Id. 17, Seq. Id. 19, Seq. Id. 21, Seq. Id. 23, Seq. Id. 25, Seq. Id. 27, Seq. Id. 29, Seq. Id. 31, Seq. Id. 33, Seq. Id. 35 and Seq. Id. 37.

In one embodiment, the invention relates the effect of a modified composition containing colloidal resveratrol nanoparticles in unconjugated form, wherein the process may further comprise use of specific designed primer sequences for analysis of expression of aforementioned genes, wherein said specified primer sequences may comprise a set of reverse primers with Seq. Id. 2, Seq. Id. 4, Seq. Id. 6, Seq. Id. 8, Seq. Id. 10, Seq. Id. 12, Seq. Id. 14, Seq. Id. 16, Seq. Id. 18, Seq. Id. 20, Seq. Id. 22, Seq. Id. 24, Seq. Id. 26, Seq. Id. 28, Seq. Id. 30, Seq. Id. 32, Seq. Id. 34, Seq. Id. 36 and Seq. Id. 38.

In one embodiment, the invention relates the effect of a modified composition containing colloidal resveratrol nanoparticles in unconjugated form on one or more genes related to insulin resistance, metabolic syndrome, aging, apoptosis, inflammation, stress resistance, cancer, cardiovascular disease, muscular dystrophy, low fertility rates or any combination thereof which may include but is not limited to genes coding for 2,4 Dienoyl-CoA reductase (DECR), Nicotinamide adenine dinucleotide phosphate (NADPH) or Glyceraldehyde 3-phosphate dehydrogenase (GAPDH), silent information regulator 1 (SIRT 1), silent information regulator 6 (SIRT 6), apolipoprotein E (APOE), lipoprotein lipase (LPL), Anti Müllerian hormone (AMH) and p53 protein, Nuclear factor NF-kappa-B p105 subunit (NFkB1), Nuclear factor of kappa light polypeptide gene enhancer in B-cells 2 (NFkB2) and Thioredoxin-interacting protein (TXINP) in mammals.

In one embodiment, the invention relates to the activation of stem cells including but not limited to VSEL, HSC, MSC, EPC etc. by a modified resveratrol composition wherein the invention first relates to a process for isolation of said stem cells. The process comprises an initial step of density gradient centrifugation obtained from peripheral blood samples of experimental subjects. In general, five healthy participants in the age range of 30-60 years were given modified resveratrol capsules orally 3 times a day for 15 days and five age-matched volunteers consumed placebo capsule orally 3 times a day for 15 days. Blood samples were collected on D0, D2 and D15 to study the effect of modified resveratrol composition on stem cells and on lipid and fasting insulin profiles. The 'buffy coat' (Pellet A, which is enriched for HSCs, MSCs and EPCs) and the RBC fraction (which is otherwise invariably discarded, Pellet B enriched for VSELs) were used to study the effect of treatment.

The said primer sequences and corresponding gene functions have been enlisted in the Table 1 below:

| Name of Transcript by qRT-PCR | Reasons to study this transcript | Primer sequences |
| --- | --- | --- |
| Oct-4A | Nuclear transcription factor responsible for pluripotent state. Primers are designed specific to exon 1 of OCT-4 gene which is exclusively present in alternatively spliced isoform OCT-4A | Forward (Seq. Id. 1) AGCCCTCATTTCACCAGGCC Reverse (Seq. Id. 2) TGGGACTCCTCCGGGTTTTG |
| Oct-4 | Total Oct-4 comprise both Oct-4A and B. Primers are designed from exon 4 and both the isoforms get amplified. OCT-4B is cytoplasmic in location and has no specific function assigned to it | Forward (Seq. Id. 3) CTTGCTGCAGAAGTGGGTGGAGGAA Reverse (Seq. Id. 4) CTGCAGTGTGGGTTTCGGGCA |
| SOX2 | One of the 3 genes that form triumvirate for pluripotent state | Forward (Seq. Id. 5) AGGAGTTGTCAAGGCAGAGAAGAGA Reverse (Seq. Id. 6) GCCGCCGCGATTGTTGTGATT |
| Nanog | One of the 3 genes that form triumvirate for pluripotent state | Forward (Seq. Id. 7) AGTCCCAAAGGCAAACAACCCACTTC Reverse (Seq. Id. 9) TGCTGGAGGCTGAGGTATTTCTGTCTC |
| Sirt 1 | Silent information regulator Sirt 1 is a NAD-dependent protein deacetylase; is a nuclear transcription regulator with ability to prevent disease and reverse aging. Have roles in energy metabolism, cell survival, DNA repair, tissue regeneration, inflammation, neuronal signaling. Resveratrol is a potent activator of Sirt1 | Forward (Seq. Id. 9) TCGCAACTATACCCAGAACATAGACA Reverse (Seq. Id. 10) CTGTTGCAAAGGAACCATGACA |
| NAMPT | The NAMPT gene encodes a protein that catalyzes the biosynthesis of nicotinamide adenine dinucleotide. (NAD). The NAD is a potent regulator of energy metabolism, and responsible for mitochondrial biogenesis, stress response and aging. | Forward (Seq. Id. 11) GCAGAAGCCGAGTTCAACATC Reverse (Seq. Id. 12) CCTTAATGTCACGCACGATTT |
| TP53 | Tumor suppressor gene responsible for DNA repair, apoptosis, cancer prevention and genomic stability. | Forward (Seq. Id. 13) ATGGAGGAGCCGCAGTCAGAT Reverse (Seq. Id. 14) GCAGCGCCTCACAACCTCCGTC |
| Ikaros | Cell surface marker for hematopoietic stem cells (HSCs) | Forward (Seq. Id. 15) CTTTCCAGTGCAACCAGTGT Reverse (Seq. Id. 16) GTGAGGCTTACCAACGGAGT |
| CD90 | Cell surface marker for mesenchymal stem cells (MSCs) | Forward (Seq. Id. 17) ACACGTGTGCACTCCACCACT Reverse (Seq. Id. 18) TGAAATCCGTGGCCTGGAGGA |
| CD14 | Cell surface marker for endothelial progenitors (EPCs) | Forward (Seq. Id. 19) AAGAGAGGTGGGGAGGTGAT Reverse (Seq. Id. 20) CAGCAGCAACAAGCAGGAC |

-continued

| Name of Transcript | Reasons to study this transcript by qRT-PCR | Primer sequences |
|---|---|---|
| PCNA | Surrogate marker to monitor proliferation. Increased expression confirms proliferation of stem cells rather than increased expression of specific transcripts in existing number of cells. | Forward (Seq. Id. 21) GATGCCGTCGGGTGAATTTG Reverse (Seq. Id. 22) TCTCTATGGTTACCGCCTCCT |
| SIRT 6 | SIRT6 locus is disrupted in cancer cell lines of the pancreas, stomach, lung, digestive tract, liver, ovary, breast, urinary tract, prostate, biliary tract, esophagus, skin, bone and endometrium with locus deletion in 35% of >1000 cancer cell lines. SIRT6 over-expression resulted in apoptosis of cervical carcinoma, fibrosarcoma, primary and metastatic breast tumor cell lines with no effect on non-transformed cell lines. | Forward (Seq. Id. 23) TTAATAAGGGAAATTTTATTGTTTT- Reverse (Seq. Id. 24) CTAACCTCAATACCC CCTAATATTC-3' |
| DECR | An accessory enzyme which participates in beta oxidation and metabolism of polyunsaturated fatty enoyl-CoA esters. Thus, this gene serves as an ideal therapeutic target for treating non-insulin dependent diabetes mellitus (NIDDM), which causes hyperglycemia due to increased fatty acid oxidation | Forward (Seq. Id. 25) CTAAGGCTATCGATAGCTATC Reverse (Seq. Id. 26) AACGGAGTTACGATCGATCGA |
| APOE | APOE gene encodes apolipoprotein E (APOE) which is a class of apolipoprotein found in the lipid profile such as chylomicron and Intermediate-density lipoprotein (IDLs). ApoE is an essential part of lipoprotein metabolism. Apolipoprotein E is a blood plasma protein responsible for the transport of lipids and cholesterol by way of interaction with the low-density lipoprotein (LDL) receptor. APOE is essential for the normal catabolism of triglyceride-rich lipoprotein | Forward (Seq. Id. 27) CCATCGATCGACCAACCAGT Reverse (Seq. Id. 28) GGTTTCCGATCGCTAGCTAGC |
| S447X | S447X gene encodes for lipoprotein lipase (LPL) which has an essential role in lipid homeostasis and energy metabolism | Forward (Seq. Id. 29) TTCGATCGCTAGCTCGGGA Reverse (Seq. Id. 30) TTTCCCGGAAATTCGGATTC |
| NFkB1 | Nuclear factor NF-kappa-B p105 subunit is a protein that in humans is encoded by the NFKB1 gene. NF-KB1 is responsible for TNF induced endothelial activation and vascular inflammation play a critical role in vascular aging and atherogenesis | Forward (Seq. Id. 31) TTCCCCGGAGCCACGATTAC Reverse (Seq. Id. 32) TAAGCGCTCCGAGCTAGCT |
| NFkB2 | Nuclear factor of kappa light polypeptide gene enhancer in B-cells 2. This gene encodes a subunit of the transcription factor complex nuclear factor-kappa-B (NFkB) which plays an important role in activation of the genes responsible for inflammation and other immune responses | Forward (Seq. Id. 33) ATGGCCCTTAGGCTACCGA Reverse (Seq. Id. 34) CCGGGCTAGATATCGCTAG |

-continued

| Name of Transcript | Reasons to study this transcript by qRT-PCR | Primer sequences |
| --- | --- | --- |
| TXINP | Thioredoxin-interacting protein in humans is encoded by the TXNIP gene. TXNIP is involved in the initiation of this destructive process of ER stress, unfolded protein, inflammation and cell death. A protein known as IRE 1 induces TXNIP causing Il-1 production and inflammation. Acts as a suppressor of tumour cell growth | Forward (Seq. Id. 35) CCAGTGTAATTCGCTAGCTAG Reverse (Seq Id. 36) AACGGAGTTCGATCGATATAT |
| GAPDH | Glyceraldehyde 3-phosphate dehydrogenase (abbreviated as GAPDH or less commonly as G3PDH) is an enzyme that catalyzes the sixth step of glycolysis and thus serves to break down glucose for energy and carbon molecules | Forward (Seq. Id. 37) TTCGAGTGGCCCACTCGAACC Reverse (Seq. Id. 38) TTACCAATCGATCGACACTAA |

Although various embodiments for synthesizing colloidally stable resveratrol nanoparticles are described in brief the preceding paragraphs, it is to be understood that this written description is not necessarily limited to the above disclosure of features or methods.

Figure 7A:
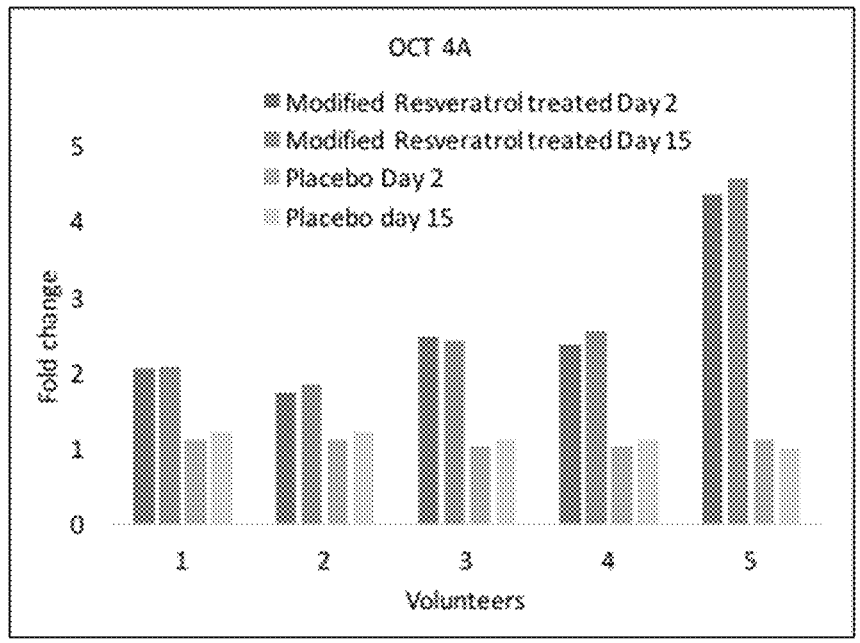
FIG. 7 illustrates effect of modified resveratrol composition induced activation of VSEL stem cells on transcripts of Oct4, Oct 4A, Nanog and Sox 2.
Figure 7:
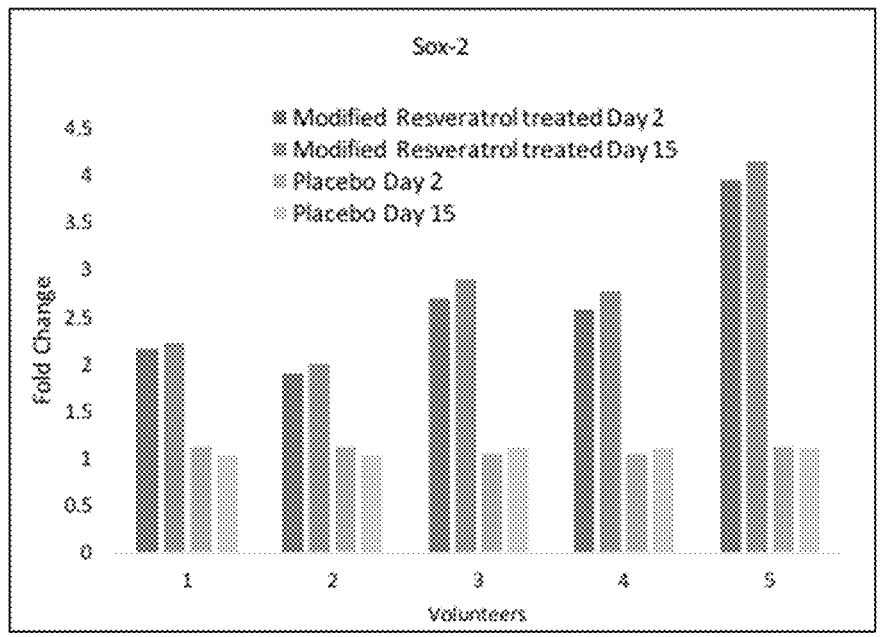
Figure 7C:
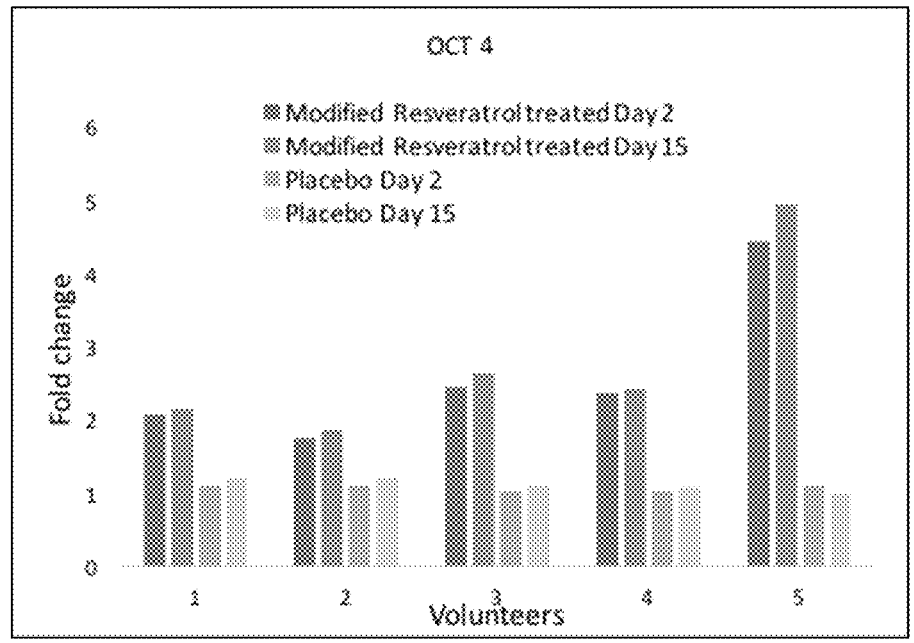
Figure 7D:
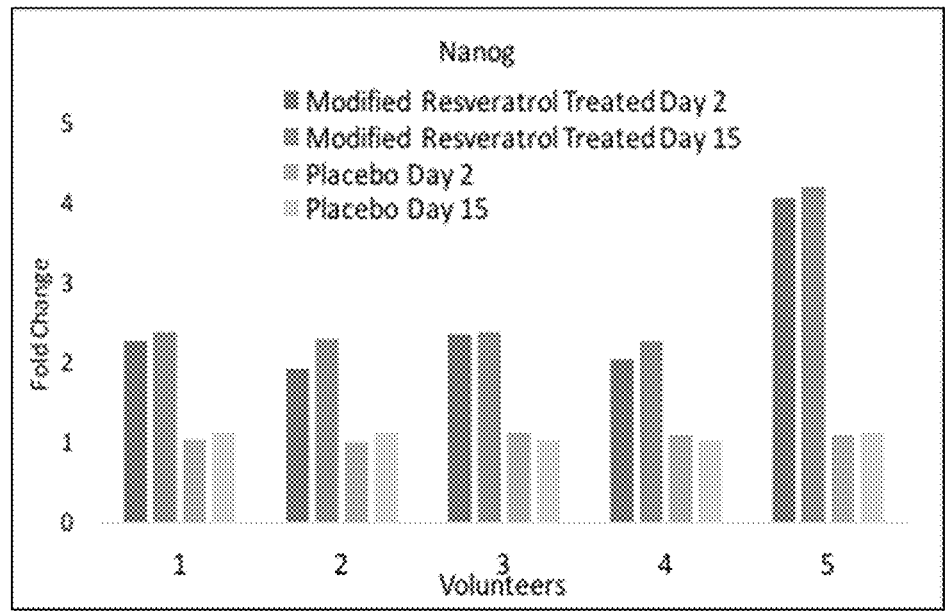
Figure 7E:
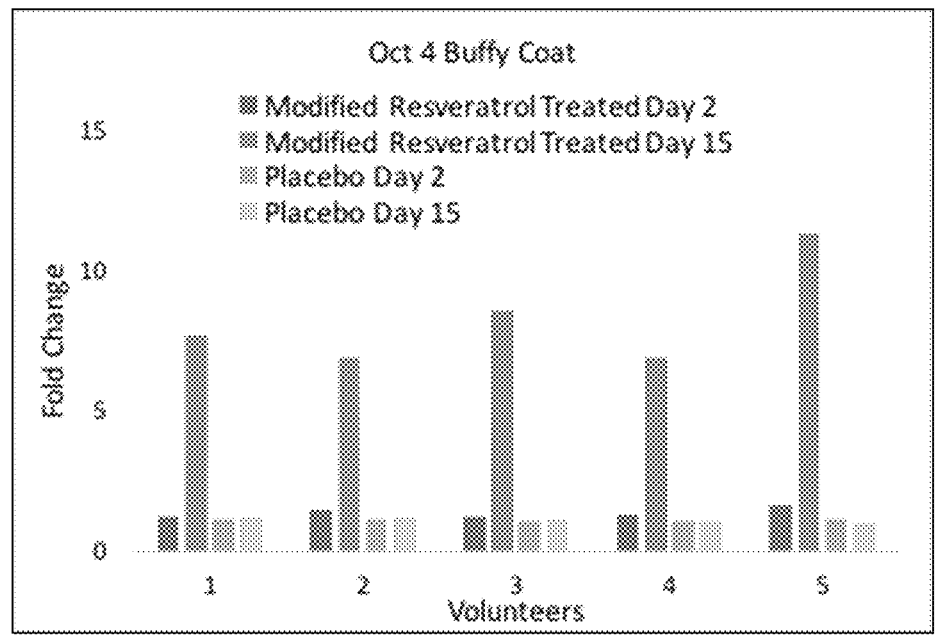
Figure 7F:
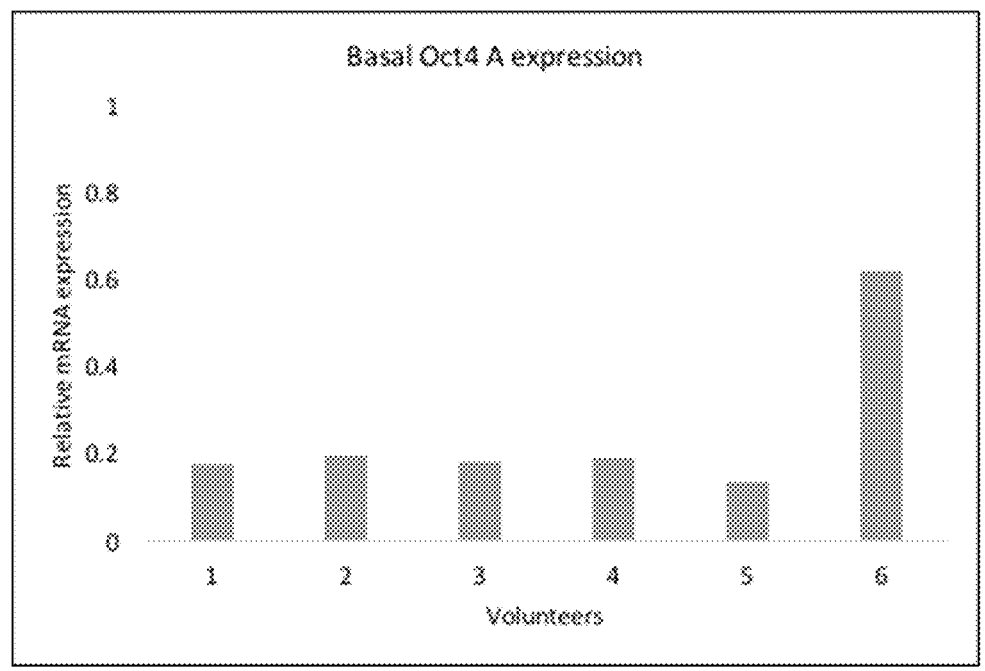
Figure 8A:
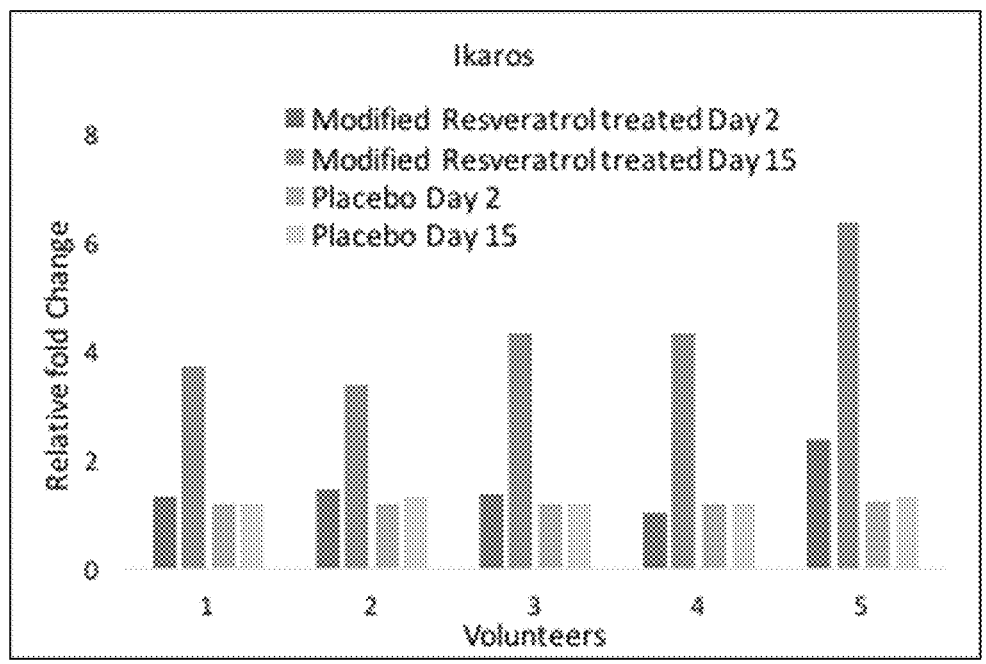
FIG. 8 illustrates effect of modified resveratrol composition induced activation of VSEL stem cells on transcripts of Ikaros, CD90 and CD14.
Figure 8B:
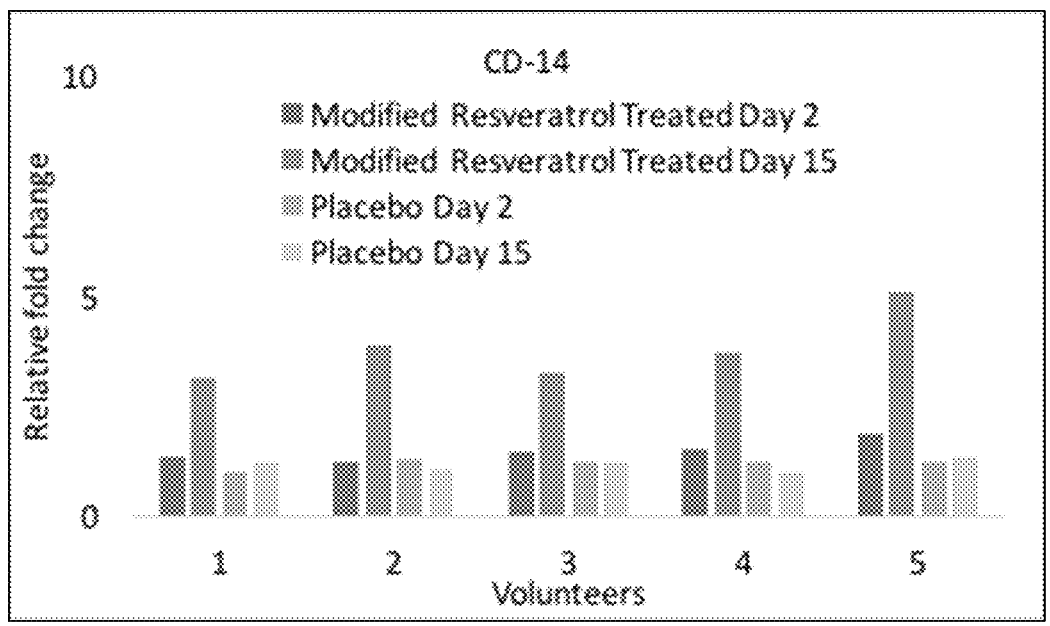
Figure 8C:
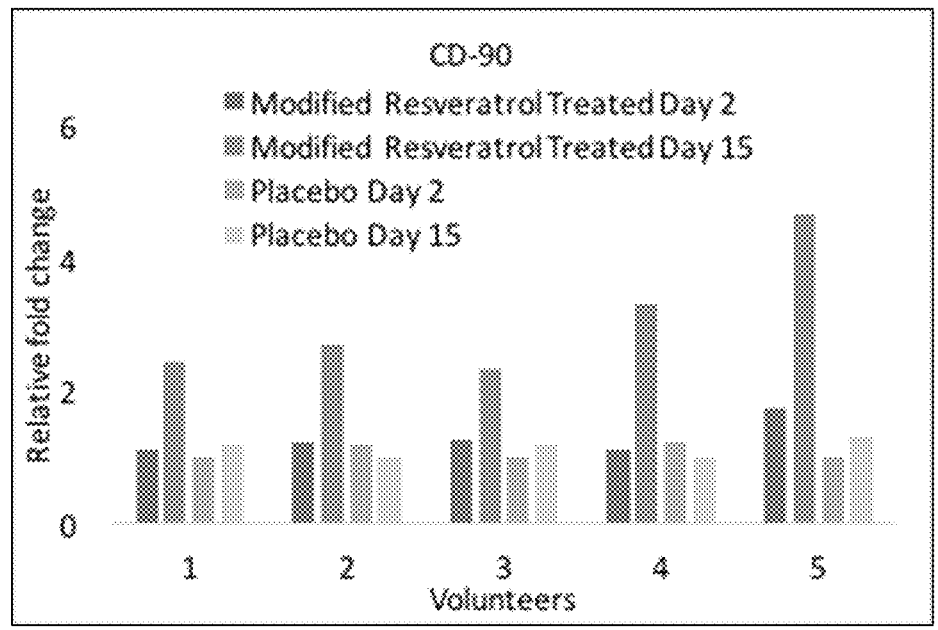
Figure 8D:
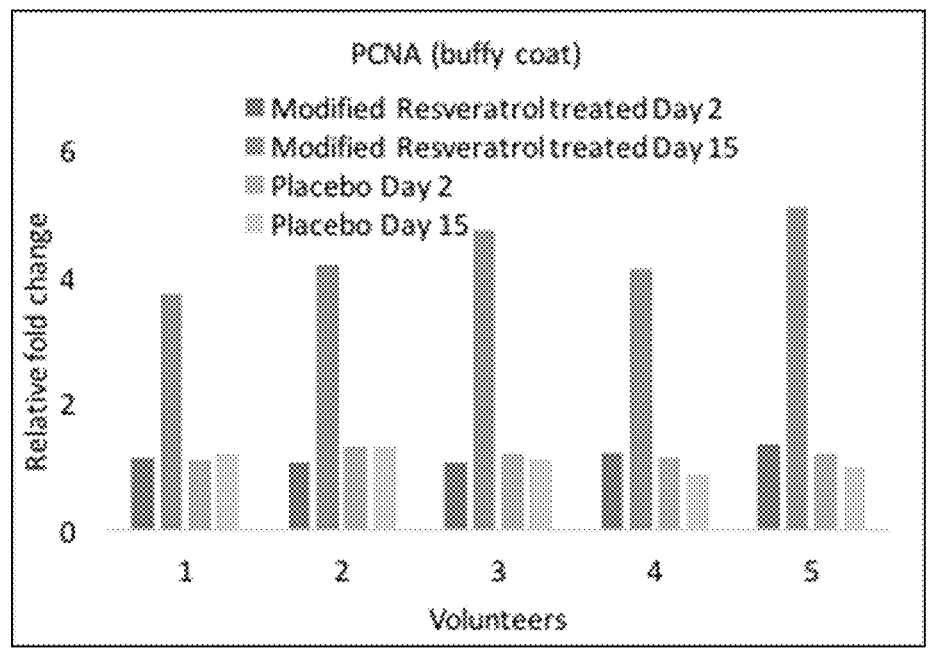
Figure 8E:
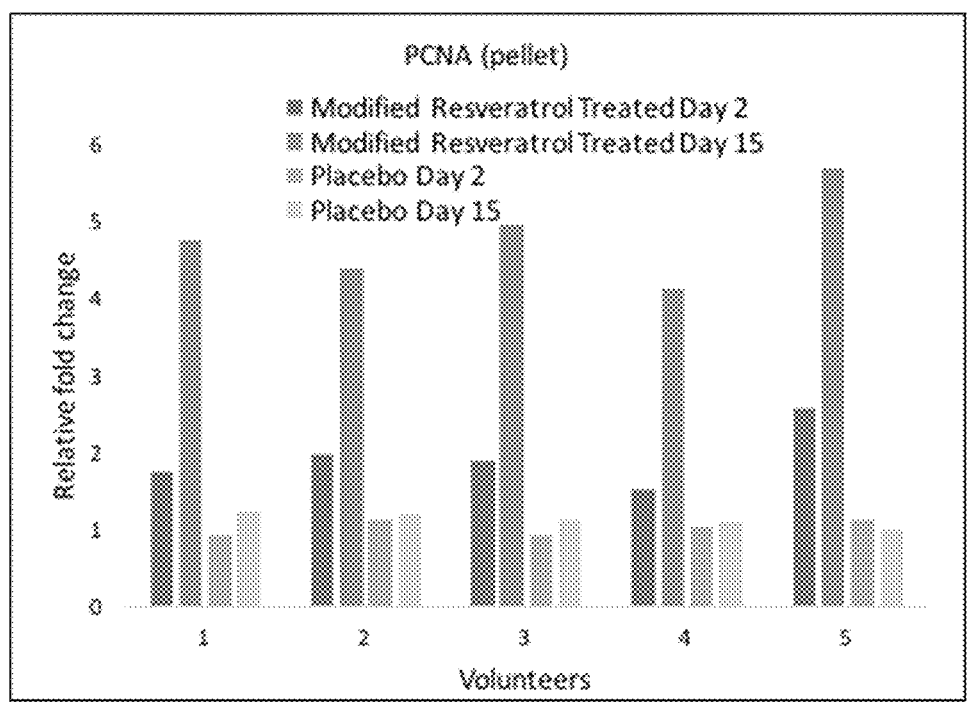
Figure 9A:
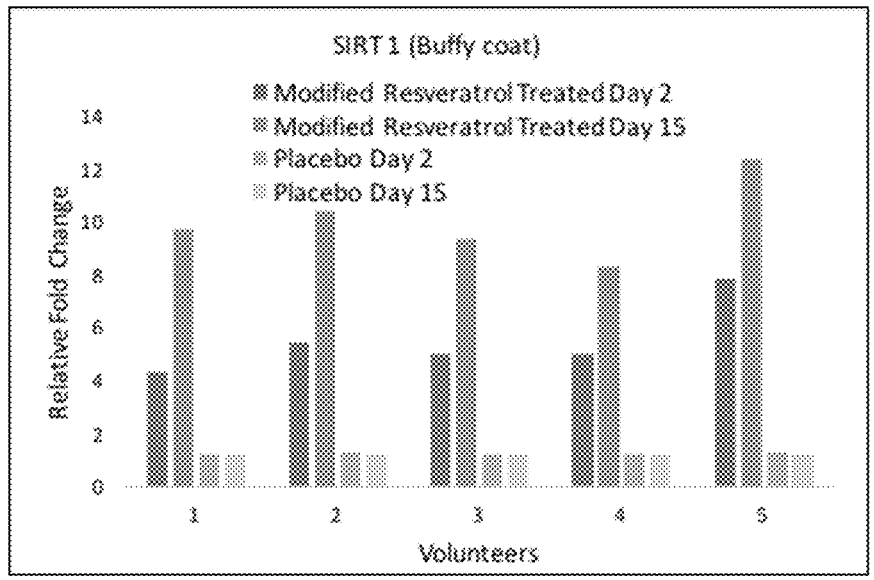
FIG. 9 illustrates effect of modified resveratrol composition induced of VSEL stem cells on transcripts of SIRT, NAMPT, p53.
Figure 9B:
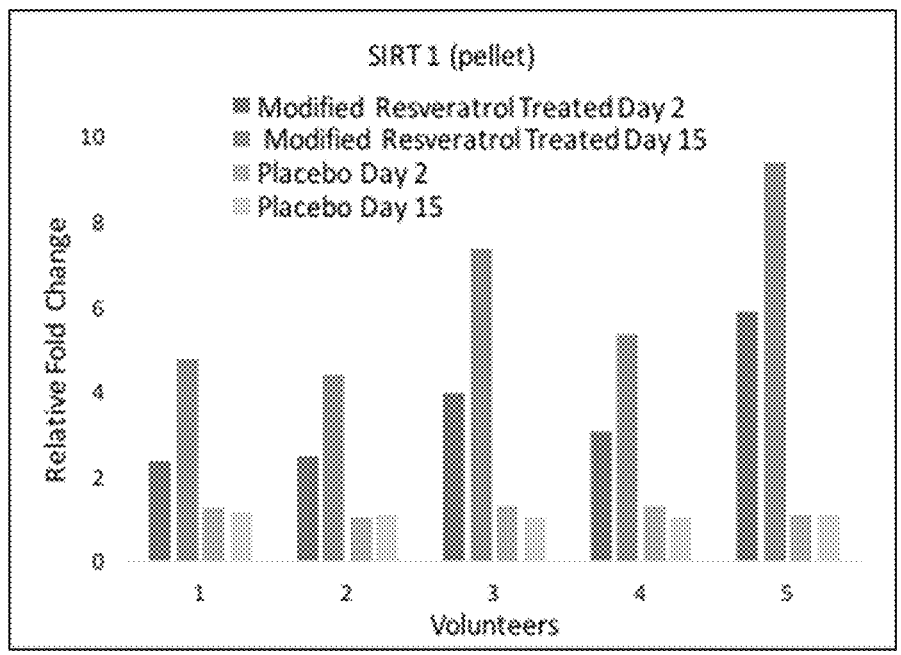
Figure 9C:
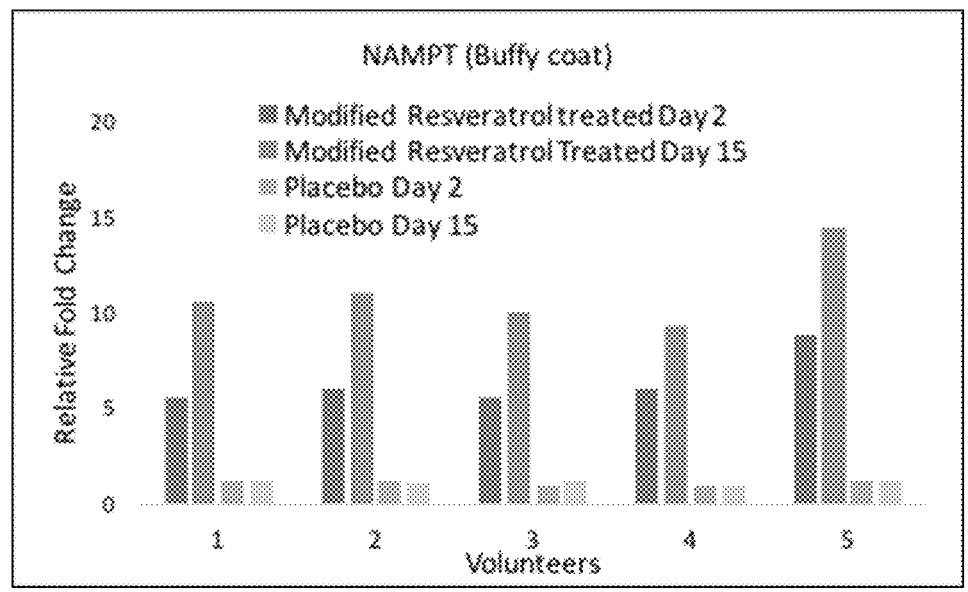
Figure 9D:
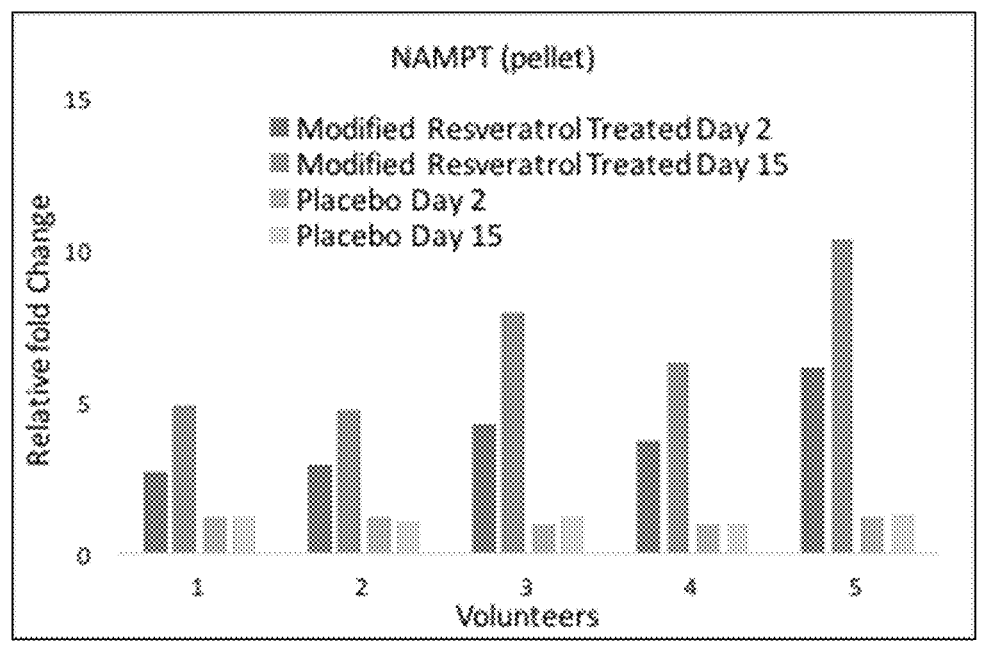
Figure 9E:
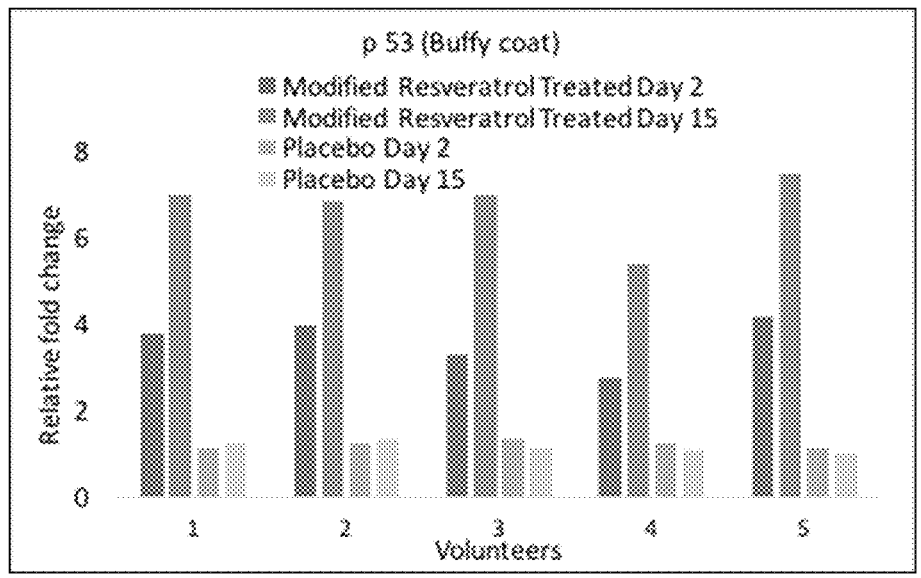
Figure 9F:
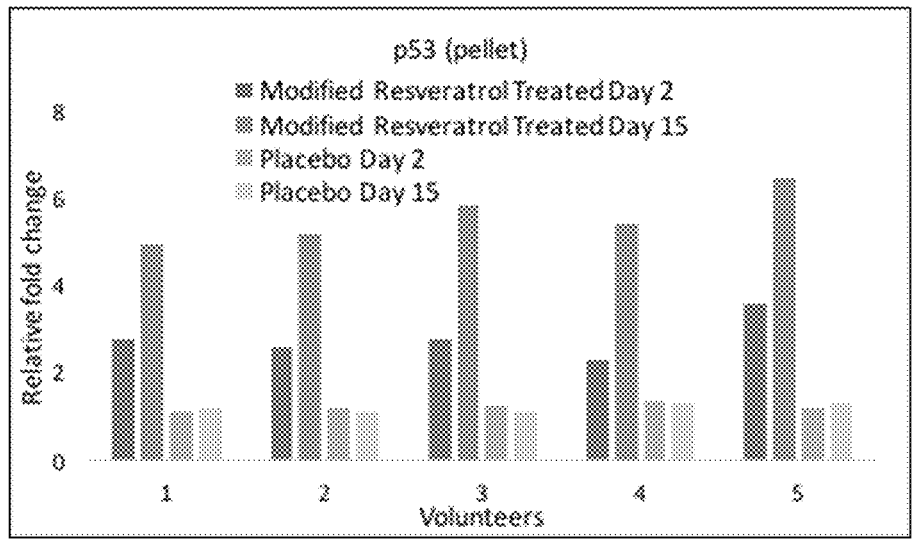

Referring to FIG. 7, in one embodiment, the invention relates to effect of modified resveratrol composition activation of VSEL stem cells as well other types of stem cells on pluripotent markers like Oct4, Oct4A, Nanog and Sox2. As evident in FIG. 7A-D, expression of Oct-4A and Oct-4 was similar in Pellet B suggesting that being pluripotent, VSELs majorly express nuclear Oct-4A and could be detected using both the set of primers. Compared to D0, all the 3 transcripts showed an almost 2-fold increase on D2 and D15 and the increase induced on D2 was sustained on D15. The 57 years old participant showed almost 4-fold increase in the expression of all 3 transcripts in agreement with the greater need for age-related rejuvenation compared to young participants. One participant was 76 years old at present and had been eating this molecule for >8 years now. It was of interest to study baseline Oct-4A mRNA expression in his peripheral blood sample. FIG. 7E shows that baseline Oct-4A expression was much higher (almost 3 folds) in his peripheral blood compared to the rest of the study participants and as expected baseline Oct-4A expression was minimal in the 57 years old participant and almost increased 4 folds compared to relatively younger participants who showed about 2 folds increase in pluripotent markers (FIG. 7A-D) after modified resveratrol composition intake. Results suggest that VSELs decrease in numbers with age and their higher numbers maintained with advanced age (by modified resveratrol composition intake) may be the basic key to longevity. The impact of treatment with modified resveratrol composition on adult stem cells in Pellet A (buffy coat obtained after density gradient centrifugation) enriched for HSCs, MSCs and EPCs was also evaluated. Almost 6-11 fold increase of total Oct-4 was observed on D2 compared to D0 (FIG. 7E) which was expected since the progenitors that arise from VSELs are expected to undergo rapid proliferation and clonal expansion. True stem cells (VSELs) self-renew by undergoing rare asymmetric cell divisions to give rise to progenitors (also termed adult stem cells) which in turn undergo symmetric cell divisions and clonal expansion (VSELs underwent self-renewal and gave rise to progenitors expressing Oct-4B and the process was greatly enhanced by modified resveratrol composition treatment. Again, the increase in Oct-4 transcript was maximum in the 57 years old aged individual. Maximum increase was observed on D15 after modified resveratrol composition treatment as it takes time for the process of differentiation to occur. Interestingly, Oct-4A transcripts were not detected in Pellet A. Adult stem cells including HSCs get separated in the buffy coat 'pellet B' which express cytoplasmic OCT-4B.

Referring to FIG. 8, in one embodiment, the invention relates to effect of modified resveratrol composition activation of VSEL stem cells on transcription of Ikaros, CD90 and CD14 which are specific transcripts for HSCs, MSCs, EPCs. FIG. 8A-C show an up-regulation of Ikaros, CD90 and CD14 which are specific transcripts for HSCs, MSCs, EPCs. Results show an up-regulation of all the three markers on D2 compared to baseline levels which were further increased on D15. Further studies need to be undertaken using multiple markers and on purified cell populations, but the results are suggestive of increased mobilization/differentiation of VSELs into their progenitors (HSCs, MSCs, EPCs) based on body requirements. In addition, Pcna expression was increased in both the VSELs (FIG. 8D) and the buffy coat (FIG. 8E) suggestive of active cell divisions associated with increased expression of various markers in response to the treatment rather than increased expression per cell.

Referring to FIG. 9, in one embodiment, the invention relates to effect of modified resveratrol composition activation of VSEL stem cells on anti-ageing related parameters, more specifically on Sirt 1, NAD, NAMPT etc. Results show up-regulation of both SIRT-1 (FIG. 9A) and NAMPT expression (FIG. 9C). Increase in expression of SIRT1 (FIG. 9B) and NAMPT (FIG. 9C) was also noticed in Pellet A thus suggesting an overall increase in the stem cells activity. Resveratrol affects SIRT1 and NAD is well documented in literature but their up-regulation occurs in VSELs is being reported for the first time in the present study. An increase in both NAD and SIRT1 in VSELs after modified resveratrol composition treatment (FIG. 9) is very interesting as it demonstrates a distinct effect of modified resveratrol composition on epigenetic status of the stem cells. Also, an increased expression of tumor suppressor gene P53 was also noticed (FIG. 9E-F).

Referring to FIG. 10, in one embodiment, the invention relates to effect of X modified resveratrol composition induced activation of VSEL stem cells on health-related parameters, more specifically on lipid and glyceride profiles of experimental subjects. A positive effect of modified resveratrol composition was noted on various serum parameters including lipid profile and insulin resistance suggestive of improved metabolism and general improvement of pancreas and cardiac function. The results provide an explanation as to why resveratrol exerts a generalized beneficial effect on wide variety of organs. VSELs are the pluripotent stem cells that serve as a backup pool to tissue-specific stem cells and exist in all the adult body organs in mice and also in humans cord blood, bone marrow, testis, ovary and other organs. Evidently, resveratrol reaches all the body organs, activates the VSELs which give rise to tissue specific stem cells and improved differentiation and thus the modified resveratrol composition appears a promising available NAD/Sirtuin/P53 activating molecule for improved, cancer-free health with advanced age.

In one embodiment, the invention relates to said modified resveratrol composition comprises up to 90% nanoparticles have a particle size less than 100 nm with a zeta potential below −20 mv in a pH range of 2 to 12 having tree fat coating. These resveratrol nanoparticles have extremely high bioavailability and increased shelf life and. They are present in colloidal form and the nanoparticles are capable of retaining stabilized and unconjugated form of resveratrol at a concentration in a range of 10000 nmoles/liter to up to 40000 nmoles/liter, with half-life of at least 3 hours when administered in mammalian body. Such highly bioavailable and high-shelf-life comprising resveratrol molecules used in the composition may alternatively be termed as eXtremely Active Resveratrol (XAR) molecules.

EXAMPLES

Below, using examples to illustrate the present invention more specifically.

However, the invention is not at all limited to the following examples. The following examples are provided by way of illustration:

Example 1—Bioavailability of Orally Administered Resveratrol

This example shows the bioavailability of orally administered resveratrol with four different systems, out of which a half-life of at least 3 hours with 1.3% of conjugated Resveratrol in plasma (Resveratrol metabolites) is achieved using a resveratrol delivery system disclosed in the disclosure. Table summarizes the comparative table of bioavailability of orally administered resveratrol by all four systems. The table shows that, when colloidally stable resveratrol nanoparticles are administered as an ingredient in a formulation, the resveratrol molecule is delivered in the free, unconjugated form at a concentration in the range of 10000 nmoles/liter to 40000 nmoles/liter in the blood plasma. Furthermore, the system is capable of retaining free unconjugated resveratrol molecule in the blood stream for up to 6 hours. This system has resulted in half-life of at least 3 hours in a human clinical study.

TABLE 2

Comparative table of bioavailability of orally administered resveratrol reported by others and our findings

| Reference | Orally administered Dose of Resveratrol | Free Resveratrol in plasma (Bioavailability) | Conjugated Unconjugated/ Resveratrol in plasma (Resveratrol metabolites) | Half-Life |
| --- | --- | --- | --- | --- |
| Goldberg et al. (2003) | 25 mg | 10 to 40 nmol/L (16 to 17% of orally administered dose of resveratrol is bioavailable) | 83 to 84% | 2 hours |
| Nguyen et al. (2009) | 5 grams | 2400 nmol/L (0.012% of orally administered dose of resveratrol is bioavailable) | 99.98% | Not reported |
| Patel et al. (2010) | 1 grams | Below the limit of quantification | 99.99% | Not reported |
| Colloidally stable resveratrol nanoparticles | 10 mg | 40,000 nmol/L (98.7% of orally administered dose of resveratrol is bioavailable) | 1.3% | At least 3 hours |

Example 2: Characterization of Coated Resveratrol Nanoparticles by Dynamic Light Scattering (DLS)

Dynamic light scattering also called as photon correlation spectroscopy determines the hydrodynamic diameter of the nanoparticles and gives information on their colloidal stability. The average hydrodynamic size recorded for the synthesized tree fat coated resveratrol nanoparticles is 103.8 nm. as shown in table 3. The polydispersity index recorded for the nanoparticles solution is 0.164. Since the polydispersity index of the tree fat coated resveratrol nanoparticle is less than 0.2; it can be inferred that the nanoparticles are monodispersed in nature i.e. all the nanoparticles are uniform in size.

TABLE 3

Dynamic light scattering: Particle size and polydispersity index of coated resveratrol nanoparticle

| | Particle size (nm) | Polydispersity Index |
| --- | --- | --- |
| resveratrol nanoparticles having tree fat coating | 103.8 | 0.164 |

Example 3: Characterization of Coated Resveratrol Nanoparticles by Zeta Potential The surface charge of the colloidally stable synthesized resveratrol nanoparticles was studied by recording the zeta potential measurements in the pH range of 2 to 12. The zeta potential was negatively charged at lower (i.e. below 2 or 2) and higher (i.e. 12 or above 12) pH as seen in FIG. 4. The trend showed that the nanoparticles were charge stabilized at both lower and higher pH. Since nanoparticles showing an absolute zeta potential value in the range of ≥−20 to −30 mV can be accepted as electrostatically stable.

Example 4: Characterization of Coated Resveratrol Nanoparticles by High Resolution Transmission Electron Microscopy (HR-TEM) and Scanning Electron Microscopy (SEM)

The most prominent method to analyze the size and shape of nanoparticles is electron microscopy. Thus, transmission electron microscopy and scanning electron microscopy was employed to determine the size and shape of resveratrol nanoparticles coated with tree fat. The SEM image (FIG. 1) revealed spherically shaped resveratrol nanoparticles. In HR-TEM the tree fat coating on resveratrol nanoparticles was clearly evident with the size ranging from 65 nm-95 nm

TABLE 4

Changes observed in the values of different parameters w.r.t baseline values.

| Sr. No | Parameters | Mean | After 15 Days treatment | After 30 Days Treatment |
|---|---|---|---|---|
| 1 | Fasting Sugar | 94.66 mg/dl | 8.0% ↓ | 5.4% ↓ |
| 2 | Post Prandial Sugar | 112.68 mg/dl | 2.6% ↓ | 8.3% ↓ |
| 3 | HOMA Index | 4.07 | 24.8% ↓ | 7.6% ↓ |
| 4 | Insulin Fasting | 18.37 µU/ml | 34.7% ↓ | 6.2% ↓ |
| 5 | Insulin Post Prandial | 40.19 µU/ml | 3.3% ↓ | 8.3% ↓ |

TABLE 5

Changes observed in the Mean values of different parameters w.r.t baseline

| Sr. No | Changes in the given Parameters | Changes After 15 Days treatment | | | Changes After 30 Days Treatment | | |
|---|---|---|---|---|---|---|---|
| | | Changes observed in the population | Maximum Increase or decrease in the value | Average Increase or decrease in the value | Changes observed in the population | Maximum Increase or decrease in the value | Average Increase or decrease in the value |
| 1 | Fasting Sugar | 60.0% ↓ | 42.4% | 10.56% | 46.7% ↓ | 33.8% | 9.89% |
| 2 | Post Prandial Sugar | 58% ↓ | 39.3% | 9.41% | 66.7% ↓ | 44.4% | 13.33% |
| 3 | HOMA Index | 76% ↓ | 84% | 40.38% | 57.8% | 81.9% | 31.78% |
| 4 | Insulin Fasting | 68% ↓ | 81.7% | 39.96% | 53.3% ↓ | 81.3% | 32.1% |
| 5 | Insulin Post Prandial | 58% ↓ | 85.9% | 47.67% | 66.7% ↓ | 92.8% | 46.06% |

(FIG. 3). The mean diameter of the synthesized tree fat coated resveratrol nanoparticles was estimated to be 80.6 nm.

Example 5

This example shows the changes in fasting sugar, post prandial sugar, insulin fasting, insulin post prandial and HOMA index in candidates after the consumption of a nutraceutical composition of 500 mg (contains active ingredient resveratrol of less than 75 mg of resveratrol). Treatment group had candidates aging between 20-53 years and mean height, weight and BMI of the candidates were within normal limits. Treatment group was asked to consume nutraceutical capsule 500 mg three times a day as per schedule at day 1 and continued to consume till day 30. Blood samples were drawn at different interval at day 0, day 15 and day 30 to find out changes in blood parameters. At day 15 of treatment, 30 cases out of 50 showed decrease in fasting sugar, 29 cases out of 50 showed decrease in Post prandial blood sugar, 34 cases out of 50 showed decrease in insulin fasting, 29 cases out of 50 showed decrease in insulin post prandial, 38 cases out of 50 showed decrease in HOMA index. At day 30 of treatment, 21 cases showed decrease in fasting sugar, 30 cases showed decrease in post prandial blood sugar, 24 cases out of 50 showed decrease in Insulin fasting, 30 cases out of 50 showed decrease in Insulin post prandial, 26 cases showed decrease in HOMA index.

Table 6 summarizes changes observed in the values of different parameters w.r.t baseline values.

This example shows the changes in serum creatinine, serum uric acid, serum calcium, testosterone, DHEA and BUN (Blood Urea Nitrogen) value in candidates after the consumption of a nutraceutical composition of 500 mg (contains active ingredient resveratrol of less than 75 mg of resveratrol).

After 15 days of treatment, 17 cases out of 50, showed increase in DHEA. After treatment of day 30, 12 cases out of 45 showed increase in DHEA.

Female Cases:

After 15 days of treatment, 10 cases out of 27 showed increase in Testosterone. After treatment at day 30, 20 cases out of 26 showed increase in Testosterone.

Male Cases:

After 15 days of treatment, 14 cases out of 23 showed increase in Testosterone.

After treatment at day 30, 13 cases out of 19 showed increase in Testosterone.

After 15 days of treatment, 14 cases out of 50 showed decrease in Serum creatinine. After treatment at day 30, 22 cases out of 45 showed decrease in Serum creatinine After 15 days of treatment, 20 cases out of 50 showed decrease in Serum uric acid. After treatment at day 30, 30 cases out of 45 showed decrease in Serum uric acid.

After 15 days of treatment, 22 cases out of 50 showed decrease in Serum calcium. After treatment at day 30, 22 cases out of 50 showed decrease in Serum calcium.

After 15 days of treatment, 26 cases out of 50 showed decrease in Blood urea nitrogen. After treatment at day 30, 27 cases out of 45 showed decrease in Blood urea nitrogen.

TABLE 6 changes observed in the values of different parameters w.r.t baseline values.

| Sr. No | Changes in the given Parameters | Changes observed in the population | Changes After 15 Days treatment — Maximum Increase or decrease in the value | Changes After 15 Days treatment — Average Increase or decrease in the value | Changes observed in the population in the value | Changes After 30 Days Treatment — Maximum Increase or decrease in the value | Changes After 30 Days Treatment — Average Increase or decrease in the value |
|---|---|---|---|---|---|---|---|
| 1 | DHEA | 34.0% ↑ | 665.7% | 97.94% | 26.7% ↑ | 1134.3% | 147.89% |
| 2 | Testosterone In Male | 37% ↑ | 1344.2% | 323.92% | 76.9% ↑ | 1299.5% | 159.38% |
| 3 | Serum Creatinine | 28% ↓ | 10.0% | 4.18% | 48.9% ↓ | 14.3% | 5.74% |
| 4 | Serum Uric Acid | 40% ↓ | 21.4% | 5.17% | 66.7% ↓ | 17.7% | 5.76% |
| 5 | Serum Calcium | 44% ↓ | 8.4% | 4.23% | 48.9% ↑ | 12.8% | 3.87% |
| 6 | Blood Urea Nitrogen | 52.0% ↓ | 54.5% | 20.82% | 60% ↓ | 50% | 19.86% |

Example 6

This example shows the changes in SIRT1 (silent mating type information regulation 2 homolog—sirtuin), 2,4 Dienoyl-CoA reductase (DECR), targeting NFKB1 (Nuclear factor NF-kappa-B p105 subunit encoder), NFKB2 (Nuclear factor NF-kappa-B p100 subunit encoder) and TP53 (gene which encodes for p53 protein) and TXNIP genes expressions in candidates after the consumption of a nutraceutical composition of 500 mg (contains active ingredient resveratrol of less than 6 mg of resveratrol). Treatment group had candidates aging between 20-53 years and mean height, weight and BMI of the candidates were within normal limits. Treatment group was asked to consume nutraceutical capsule 500 mg three times a day as per schedule at day 1 and continued to consume till day 30 Blood samples were drawn at different interval at day 0, day 15 and day 30 to find out changes in blood parameters. Table 4 summarizes, Changes observed in observed in gene expressions of 5 different candidates at Day 15 Vs. Day 0 and Day 30 Vs. Day 0. Sample 2 shows upregulation of DECR at day 15 of the treatment. All the samples except sample 4 show, down-regulation of NFKB1 in whole treatment. Sample 1 and 5 show downregulation of NFKB2 in whole treatment. Sample 1,4 and 5 show regulation of SIRT1 in whole treatment. Sample 2 shows regulation of TP53 at day 15 of the treatment. All samples show downregulation of TXNIP in whole treatment. Results for each comparison are given in the table below as 'Fold Change' values indicating the folds of change in expression with respect to reference. In the case of down-regulated genes, fold changes have been denoted with negative sign. For example, a fold change value of −2.14 in Day 15 vs. Day 0 indicates that the gene is 2.14 fold down-regulated in Day 15 compared to Day 0.

Example 7—Elevation or Demotion in the Lipid Profile Level

This example shows the changes in HDL, LDL, VLDL, Total cholesterol, Cholesterol HDL ratio, LDL/HDL ratio and triglycerides in candidates after the consumption of a nutraceutical composition of 500 mg (contains active ingredient resveratrol of less than 6 mg of resveratrol). Treatment group have candidates aging between 20-53 years and Mean height, weight and BMI of the candidates were within normal limits. Treatment group asked to consume nutraceutical capsule 500 mg three times a day as per schedule at day 1 and will continue to consume till day 30. Blood samples will be drawn at different interval at day 0, day 15 and day 30 to find out changes in blood parameters. At day 15, 18 cases out of 50 showed increase in HDL level; 22 cases out of 50 showed decrease in LDL level; 25 cases out of 50 showed decrease in total cholesterol level; 27 cases out of 50 showed decrease in VLDL level; 27 cases out of 50 showed decrease in Triglycerides level; 21 cases showed decrease in cholesterol/HDL ratio; 21 cases out of 50 showed decrease in LDL/HDL ratio. At day 30, 14 cases out of 50 showed increase in HDL level; 23 cases out of 50 showed decrease in LDL level; 27 cases out of 50 showed decrease in total cholesterol level 28 cases out of 50 showed decrease in VLDL level; 28 cases out of 50 showed decrease in Triglycerides level; 17 cases out of showed decrease in cholesterol/HDL ratio; 15 cases out of 50 showed decrease in LDL/HDL ratio.

TABLE 7

Changes observed in the values of different parameters w.r.t baseline values.

|  |  | Changes After 15 Days treatment | | | Changes After 30 Days Treatment | | |
| --- | --- | --- | --- | --- | --- | --- | --- |
| Sr. No | Changes in the given Parameters | Changes observed in the population | Maximum Increase or decrease in the value | Average Increase or decrease in the value | Changes observed in the population in the value | Maximum Increase or decrease in the value | Average Increase or decrease in the value |
| 1 | HDL Cholesterol | 36.0% ⬆ | 27.3% | 8.53% | 31.1% ⬆ | 26.9% | 8.47% |
| 2 | Total Cholesterol | 50% ⬇ | 19.9% | 6.16% | 60% ⬇ | 22.4% | 7.77% |
| 3 | LDL | 44% ⬇ | 27.5% | 7.03% | 51.1% ⬇ | 36.4% | 8.44% |
| 4 | VLDL | 54% ⬇ | 61.1% | 24.86% | 62.2% ⬇ | 57.6% | 24.57% |
| 5 | Triglycerides | 54% ⬇ | 61.1% | 24.87% | 62.2% ⬇ | 57.6% | 24.57% |
| 6 | Cholesterol/ HDL ratio | 42% ⬇ | 20% | 7.04% | 37.8% ⬇ | 26.9% | 6.82% |
| 7 | LDL/HDL Ratio | 42% ⬇ | 21.1% | 7.68% | 33.3% ⬇ | 21.3% | 7.86% |

Example 8

This example shows the changes APOE and LPL in candidates after the consumption of a nutraceutical composition of 500 mg (contains active ingredient resveratrol of less than 6 mg of resveratrol). Treatment group have candidates aging between 20-53 years and Mean height, weight and BMI of the candidates were within normal limits. Treatment group asked to consume nutraceutical capsule 500 mg three times a day as per schedule at day 1 and will continue to consume till day 30. Blood samples will be drawn at different interval at day 0, day 15 and day 30 to find out changes in blood parameters.

Example 9—Elevation in the AMH Level

This example shows the changes in AMH in female candidates after the consumption of a Nutraceutical composition of 500 mg (contains active ingredient resveratrol of less than 6 mg of resveratrol). Treatment group will be asked to consume Nutraceutical capsule 500 mg three times a day as per schedule at day 1 and will continue to consume till day 30. Blood samples will be drawn at different interval at day 0 and day 30 to find out changes in AMH levels. At day 30, 7 cases out of 26 (26.9%) showed increase in AMH, Maximum of 68.2% with an average of 38.39%. Table 8 summarizes, the changes in the AMH level after 30 days of resveratrol consumption.

TABLE 8

Proportion of the sample amounting to changes in the AMH level

| | | Changes After 30 Days Treatment | | |
| --- | --- | --- | --- | --- |
| Changes in the given Parameters | Number of patients | Changes observed in the population in the value | Maximum Increase or decrease in the value | Average Increase or decrease in the value |
| Baseline AMH | 26 | | | |
| | 7 | 26.9% ⬆ | 68.2% | 38.39% |
| | 15 | 15.38% NC | | |

Example 10

This example shows the changes in mean Estradiol (pg/ml) in female candidates after the consumption of a Nutraceutical composition of 500 mg (contains active ingredient modified resveratrol of less than 75 mg of resveratrol).

Treatment group will be asked to consume Nutraceutical capsule 500 mg three times a day as per schedule at day 1 and will continue to consume till day 30. Blood samples will be drawn at different interval at day 0 and day 30 to find out changes in blood parameters.

Estradiol After 30 days of treatment, mean Estradiol showed significant rise of 98.3% from baseline. Table 9 summarizes, the changes in the Estradiol level at Day 30 compared to the respective basal reading after of resveratrol consumption.

TABLE 9

Changes observed in the mean values of the Estradiol

| Parameters | Mean | After 30 Days Treatment |
| --- | --- | --- |
| Estradiol | 41.71 pg/ml | ⬇ 98.3% |

After day 30, 39 cases out of 45 (86.7%) showed increase in Estradiol.

Table 10 summarizes, the changes in the Estradiol level after 30 days of resveratrol consumption.

TABLE 10

Proportion of the sample amounting to changes in the Estradiol level.

| | | Changes After 30 Days Treatment | | |
| --- | --- | --- | --- | --- |
| Changes in the given parameters | Number of patients | Changes observed in the population in the value | Maximum Increase or decrease in the value | Average Increase or decrease in the value |
| Baseline Estradiol (in females) | 45 | | | |
| | 39 | 86.7% ⬆ | 1185.8% | 204.38% |

Example 11

This example shows the effect of treatment on high-density lipoproteins (HDL), Dehydroepiandrosterone (DHEA), weight and Hamilton anxiety in candidates after the consumption of a nutraceutical composition of 500 mg (contains active ingredient resveratrol up to 75 mg of resveratrol). Treatment group had candidates total 12 subjects including six cancer and six healthy volunteers aged between 25 and 65 years of either sex were included in the study. Cancer patients, at terminal stage of the disease; undergoing different cycles of chemotherapy and healthy subjects, who were not taking any regular medication or supplementation, having normal or less than normal range of HDL level were selected. Treatment group was asked to consume nutraceutical capsule 500 mg six times a day as per schedule at day 1 and continued to consume till day 30. In cancer group, initially, two patients out of six were given only topical Resveratrol for seven days because they were unable to take anything orally. Rest of the four patients in cancer group and all patients in healthy group were given topical Resveratrol three times a day (morning, evening and night) [In one litre water 30 g of salt 7 containing about 5 mg of Resveratrol was used as a swab on the whole body] and 6 capsules a day. The nutraceutical composition containing resveratrol has shown positive results in the human trials on terminal cases of cancer. The results of pilot study indicated improvement in quality of life all aspects in all subjects. Unwanted effects of chemotherapy such as cramps, joint pain, nausea, indigestion were reduced considerably. Energy levels increased in all patients. Quality and quantity of sleep was improved. There was a noticeable change in Hamilton's anxiety scale in four patients. Three patients had weight gain and two patients had weight loss. There was no general trend as far as weight is considered. Dehydroepiandrosterone (DHEA) is produced by the adrenal glands and used by the body for estrogen and testosterone production. Blood levels of DHEA rise until they peak in the third decade of life, then rapidly decline. In cancer patients, we found significant increase in the levels of DHEA, post oral Resveratrol administration. Hamilton rating score in each cancer patient was assessed during the study which indicates the anxiety level, we found that there was significant decrease in the Hamilton anxiety score. In healthy subjects, we found that there was a significant increase in the DHEA and HDL levels.

Example 12

This example shows the changes imposed by the treatment in the gene expression levels in vivo in human subjects after administration of the nutraceutical composition containing resveratrol using real-time PCR. In all, 8 genes were studied viz. p53, NFκB2, NFκB1, SIRT1, DECR, APOE, S447X, and NADPH. POC gene study was conducted to test for impact on 8 specific genes. Healthy subjects of age between 20 and 55 years of either sex who were not taking any regular medication or supplementation, having normal or less than normal range of HDL level. The study was carried out for a treatment period of 30 days during which the subject were asked consumed the consumption of a nutraceutical composition of 500 mg (contains active ingredient resveratrol up to 75 mg of resveratrol) 6 times a day. Anti-cancer action of resveratrol can broadly be viewed and studied in four simultaneously acting mechanisms viz. a) Toxic to cancer cells; b) Chemo-protective to healthy cells surrounding the tumor; c) Rejuvenating and immunity enhancing to noncancerous normal cells; d) Modulations in gene expression, as shown in Table 11 and Table 12. Thereby restoring the p53 activity for apoptosis in cancer cells.

TABLE 11

Studies indicating four simultaneous therapeutic actions of resveratrol in cancer

| Actions of Resveratrol | Compilation of Previous Studies | | |
|---|---|---|---|
| | In vitro Studies | Animal Studies | Human Trials |
| Toxic to cancer cells | (Bai et al. 2010; Subramanian et al. 2010) (1, 2) | (Baur and Sinclair 2006; Bishayee 2009) (3, 4) | (Bishayee 2009; Tomé-carneiro et al. 2013) (4, 5) -Not Successful |
| Chemo-protective to healthy cells around tumor | (Aziz et al. 2003; Brisdelli et al 2009; Hosoda et al. 2013; Abdel-latif et al. 2015) (6-9) | (Jang et al. 1997; Aziz et al. 2003; Baur and Sinclair 2006) (3, 9-10) | — |
| Vigorous to rest of the 70 trillion non-cancer, normal cells, each is getting the simultaneous effects of immunity enhancement and rejuvenation. This higher immunity ensures prevention of aging disease (Vaccine action) | (Mukherjee et al. 2010; Gambini et al. 2015) (11, 12) | (Gambini et al. 2015) (12) | (Goldberg et al. 2003; Tomé-carneiro et al. 2013; Gambini et al. 2015) (5, 12, 13) - Not Successful |

TABLE 11-continued

Studies indicating four simultaneous therapeutic actions of resveratrol in cancer

| Actions of Resveratrol | Compilation of Previous Studies | | |
|---|---|---|---|
| | In vitro Studies | Animal Studies | Human Trials |
| Modulations in gene expression | (She et al. 2003; Cecchinato et al. 2007; Fukui et al. 2010; Oi et al. 2014) (14-17) | (Owaga and Sakhile 2014; Wang et al. 2015; Yang et al. 2015) (18-20) | — |

TABLE 12

Studies indicating four simultaneous therapeutic actions of the nutraceutical composition containing resveratrol in cancer

| Actions of Resveratrol | The nutraceutical composition containing resveratrol | |
|---|---|---|
| | Animal Studies | Human Trials |
| Toxic to cancer cells | — | Increase in body weight in 60% patients, energy level and decrease in Hamilton's Anxiety Score in all patients |
| Chemo-protective to healthy cells around tumor | — | Increase in body weight, energy level and decrease in Hamilton's Anxiety Score |
| Vigorous to rest of the 70 trillion non-cancer, normal cells, each is getting the simultaneous effects of immunity enhancement and rejuvenation. This higher immunity ensures prevention of aging disease (Vaccine action) | Safe at the dose of 2000 mg/kg body weight in rats | Increase in HDL and DHEA-immunity marker |
| Modulations in gene expression | — | **Activation of p53, upregulation of NFκB and DECR |

Example 13

The bioavailability of modified resveratrol and its modulation on SIRT1 gene, serum creatinine kinase levels and effect of nutraceutical and pharmaceutical composition containing modified resveratrol on Muscular Dystrophy patients is assessed by conducting human clinical trial. This is a single-centric, open-label-study, designed to determine the bioavailability of modified resveratrol in 6 healthy patients. Healthy male or female volunteers aged 25-80 years were included in the clinical trial. Treatment group was asked to consume 500 mg nutraceutical capsule containing up to 75 mg of Resveratrol. Blood samples of the volunteers were collected at several intervals (0.25 hr, 0.5 hr, 1.00 hr, 2.00 hr and 6.00 hr) post capsule consumption, to find out the concentration of unconjugated resveratrol in the plasma sample. The plasma samples of the patients were subjected to LC-MS/MS analysis and the concentration of unconjugated resveratrol at various time-points was assessed. The LC-MS/MS results showed the presence of unconjugated resveratrol in the plasma of all the volunteers, with a half-life of three hours and a concentration of up to 40,000 nM/L.

TABLE 13

Comparative table of the modified Resveratrol, Synthetic resveratrol and Japanese Knotweed

| Plasma level | Conjugate/ Free Half | life in blood | Synthetic/ Natural | Delivery system |
|---|---|---|---|---|
| 5-40 nmol/liter | Conjugate | 30 min | Synthetic | Oral |
| 2-5 nmols/liter | Conjugate | Untested | Natural | Oral |
| Upto 40,000 nmols/liter | Free molecules | 3 hours | Plant produced | Oral and Topical |

Example 14

The example shows the changes in blood parameters and SIRT1 gene expression in candidates after the consumption of the nutraceutical composition of 500 mg (contains active ingredient resveratrol up to 75 mg of resveratrol). Treatment group had candidates aging between 20-55 years of either sex who were not taking any regular medication or supplementation, having normal or less than normal range of HDL level. Treatment group was asked to consume the nutraceutical capsule 500 mg six times a day as per schedule at day 1 and continued to consume till day 30. Blood samples were drawn at different interval at day 0, day 15 and day 30 to find out changes in blood parameters. Creatinine (Kidney):

Reduction in Creatinine levels (48.9%) have shown a very positive effect in a significant number of volunteers in 30 days. SIRT1 gene and p53 gene has up-regulated in a significant number of volunteers in 30 days.

The foregoing description shall be interpreted as illustrative and not in any limiting 25 sense. A person of ordinary skill in the art would understand that certain modifications could come within the scope of this disclosure.

I claim:

1. A resveratrol delivery system comprising a modified resveratrol composition, wherein, said modified resveratrol composition comprises colloidally stable resveratrol nanoparticles having a jackfruit tree fat coating, characterized in that said modified resveratrol composition when administered to a mammal suffering from insulin resistance, metabolic syndrome, aging, inflammation, stress resistance, cancer, cardiovascular disease, muscular dystrophy, low fertility rates or any combination thereof in a predetermined therapeutically effective amount, a) upregulates expression of genes comprising such genes coding for 2,4 Dienoyl-CoA reductase (DECR), Nicotinamide adenine dinucleotide phosphate (NADPH), silent information regulator 1 (SIRT 1), silent information regulator 6 (SIRT 6), apolipoprotein E (APOE), lipoprotein lipase (LPL), Anti Müllerian hormone (AMH) or p53 protein in mammals, and b) downregulates expression of genes comprising such genes coding for Nuclear factor NF-kappa-B p105 subunit (NFkB1), Nuclear factor of kappa light polypeptide gene enhancer in B-cells 2 (NFkB2) or Thioredoxin-interacting protein (TXINP) in mammals, further characterized in that, said modified resveratrol composition comprises up to 90% nanoparticles having the jackfruit tree fat coating and having a particle size less than 100 nm with a zeta potential below −20 mv in a pH range of 2 to 12, wherein the nanoparticles are capable of retaining stabilized and unconjugated form of resveratrol at a concentration in a range of 10000 nmoles/liter to up to 40000 nmoles/liter, with a half life of at least 3 hours when administered in a mammalian body.

2. The resveratrol delivery system according to claim 1, wherein said modified resveratrol composition comprises resveratrol from natural sources.

3. The resveratrol delivery system according to claim 1, wherein said modified resveratrol composition decreases fasting sugar, post-prandial sugar, fasting insulin, post prandial insulin and HOMA index at end of a treatment period of a predetermined number of days.

4. The resveratrol delivery system according to claim 1, wherein said modified resveratrol composition decreases serum creatinine, serum uric acid and BUN (Blood Urea Nitrogen) and positively modulates serum creatinine kinase value at end of a treatment period of a predetermined number of days.

5. The resveratrol delivery system according to claim 1, wherein said modified resveratrol composition downregulates TXNIP gene and prevents death of beta cells or loss of their function against mitochondria-mediated-apoptosis at end of a treatment period of a predetermined number of days.

6. The resveratrol delivery system according to claim 1, wherein said modified resveratrol composition increases a Dehydroepiandrosterone (DHEA) level at end of a treatment period of a predetermined number of days.

7. The resveratrol delivery system according to claim 1, wherein said modified resveratrol composition improves the Anti-mullerian hormone (AMH) and estradiol levels and increases the yield of healthy oocytes, facilitating embryo implantation to a uterine wall during in-vitro fertilization procedures at end of a treatment period of a predetermined number of days.

8. The resveratrol delivery system according to claim 1, wherein said modified resveratrol composition suppresses cellular proliferation by induction of apoptosis through Fas/CD95, mitochondrial and p53 mediated pathways at end of a treatment period of a predetermined number of days.

9. The resveratrol delivery system according to claim 1, wherein said modified resveratrol composition reduces fasting insulin level, TG (Triglyceride) level, Total Cholesterol content, Very-Low-Density-Lipoprotein (VLDL) level and Cholesterol: High Density Lipoprotein (HDL) level and elevates High Density Lipoprotein (HDL) level at end of a treatment period of a predetermined number of days.

10. The resveratrol delivery system according to claim 1, wherein said predetermined therapeutically effective amount is obtained by administering said resveratrol delivery system three times a day for thirty days, characterized in that each dose of 500 mg contains active ingredient resveratrol of less than 75 mg of resveratrol, or by administering said resveratrol delivery system six times a day for thirty days, characterized in that each dose of 500 mg contains active ingredient resveratrol of less than 75 mg of resveratrol.

11. A process for synthesizing a modified resveratrol composition for use in resveratrol delivery system, said process comprising the steps of:
   a) selecting matured kernels that contain resveratrol;
   b) germinating the matured kernels by soaking them in a nutrient medium for a prescribed period of 11 days by maintaining a predefined temperature and a varying magnetic strength to enhance the resveratrol content in the kernels;
   c) drying the sprouted kernels for 1 day, wherein critical cycles of temperatures are maintained;
   d) crushing the dried kernels and obtaining purified resveratrol molecules for preparing a formulation having colloidally stable resveratrol nanoparticles;
   e) coating resveratrol molecules with a jackfruit tree fat, to form colloidally stable resveratrol nanoparticle by incubating the resveratrol nanoparticle with the jackfruit tree fat under constant mechanical stirring, for a predefined period of time;
   wherein up to 90% coated nanoparticles having a particle size less than 100 nm, characterized in that the nanoparticles are capable of retaining stabilized and unconjugated form of resveratrol at a concentration in a range of 10000 nmoles/liter to 40000 nmoles/liter, with a half life of at least 3 hours when administered in a mammalian body, further characterized in that, said process results in a resveratrol delivery system that,
   i) upregulates expression of genes comprising such genes coding for 2,4 Dienoyl-CoA reductase (DECR), Nicotinamide adenine dinucleotide phosphate (NADPH) or silent information regulator 1 (SIRT 1), silent information regulator 6 (SIRT 6), apolipoprotein E (APOE), lipoprotein lipase (LPL), Anti Müllerian hormone (AMH) and p53 protein in mammals, and
   ii) downregulates expression of genes comprising such genes coding for Nuclear factor NF-kappa-B p105 subunit (NFkB1), Nuclear factor of kappa light polypeptide gene enhancer in B-cells 2 (NFkB2) and Thioredoxin-interacting protein (TXINP) in mammals, when administered in a mammalian body.

12. A resveratrol delivery system comprising a modified resveratrol composition, wherein, said modified resveratrol composition comprises colloidally stable resveratrol nanoparticles having a jackfruit tree fat coating as a first active ingredient and a second active ingredient comprising a pyridinecarboxylic acid with the general formula $C_6H_5NO_2$, characterized in that said modified resveratrol composition administered to a mammal in a predetermined therapeutically effective amount, activates very small embryonic like (VSEL) stem cells, hematopoietic stem cell (HSC), mesenchymal stem cells (MSC), Endothelial progenitors cell (EPC), murine very small embryonic like (muVSEL), or any combination thereof, further characterized in that, said modified resveratrol composition comprises colloidally stable resveratrol nanoparticles having the jackfruit tree fat coating, and having a particle size less than 100 nm with a zeta potential below −20 mv in a pH range of 2 to 12, such that the nanoparticles are capable of retaining stabilized and unconjugated form of resveratrol at a concentration in a range of 10000 nmoles/liter to 40000 nmoles/liter, with a half life of at least 3 hours when administered in a mammalian body.

13. The resveratrol delivery system according to claim 12, wherein said modified resveratrol composition comprises resveratrol from natural sources.

14. The resveratrol delivery system according to claim 12, wherein said modified resveratrol composition upregulates expression of genes coding marker proteins comprising octamer-binding transcription factor 4 (Oct4 and Oct 4A), NANOG transcription factor, SRY (sex determining region Y)-box 2 (Sox 2), Ikaros family zinc finger protein 1, Cluster Differentiation 90 protein, Cluster Differentiation 14 protein, or any combination thereof at end of a treatment period of a predetermined number of days.

15. The resveratrol delivery system according to claim 12, wherein said modified resveratrol composition upregulates expression of Silent Information Regulator—1 (SIRT-1), Nicotinamide phosphoribosyltransferase (NAMPT), Proliferating cell nuclear antigen (PCNA) and tumor suppressor protein (TP53) at end of a treatment period of a predetermined number of days.

16. The resveratrol delivery system according to claim 12, wherein said modified resveratrol composition is administered as a pharmaceutical formulation three times a day for thirty days, characterized in that each dose of 500mg contains active ingredient resveratrol of less than 75 mg of resveratrol.

17. The resveratrol delivery system according to claim 12, wherein said modified resveratrol composition activates a hematopoietic system by promoting self-renewal of pluripotent VSELs and their differentiation into HSCs, MSCs and EPCs.

18. The resveratrol delivery system according to claim 12, wherein said colloidally stable resveratrol nanoparticles are synthesized by a process comprising the steps of:
   a) selecting matured kernels that contain resveratrol;
   b) germinating the matured kernels by soaking them in a nutrient medium for a prescribed period of 11 days by maintaining a predefined temperature and a varying magnetic strength to enhance the resveratrol content in the kernels;
   c) drying the sprouted kernels for 1 day, wherein critical cycles of temperatures are maintained;
   d) crushing the dried kernels and obtaining purified resveratrol molecules for preparing a formulation having colloidally stable resveratrol nanoparticles;
   e) coating resveratrol molecules with a jackfruit tree fat, to form colloidally stable resveratrol nanoparticle by incubating the resveratrol nanoparticle with the jackfruit tree fat under constant mechanical stirring, for a predefined period of 24 hours; wherein up to 90% coated nanoparticles having a particle size less than 100 nm, characterized in that the nanoparticles are capable of retaining stabilized and unconjugated form of resveratrol at a concentration in a range of 10000 nmoles/liter to 40000 nmoles/liter, with a half-life of at least 3 hours when administered in a mammalian body.

19. The resveratrol delivery system of claim 2, wherein the natural source is peanut skin.

20. The resveratrol delivery system of claim 13, wherein the natural source is peanut skin.

* * * * *